US008557738B2

(12) United States Patent
Mitani et al.

(10) Patent No.: US 8,557,738 B2
(45) Date of Patent: Oct. 15, 2013

(54) NITROGEN-CONTAINING HETEROCYCLIC DERIVATIVE AND FUNGICIDE FOR AGRICULTURAL AND HORTICULTURAL USE

(75) Inventors: Akira Mitani, Kanagawa (JP); Jun Inagaki, Kanagawa (JP); Raito Kuwahara, Kanagawa (JP); Masahiro Yokoyama, Kanagawa (JP); Kotaro Shibayama, Kanagawa (JP); Motoaki Sato, Kanagawa (JP)

(73) Assignee: Nippon Soda Co., Ltd., Tokyo (JP)

( * ) Notice: Subject to any disclaimer, the term of this patent is extended or adjusted under 35 U.S.C. 154(b) by 214 days.

(21) Appl. No.: 13/058,273

(22) PCT Filed: Aug. 10, 2009

(86) PCT No.: PCT/JP2009/003845

§ 371 (c)(1),
(2), (4) Date: Feb. 9, 2011

(87) PCT Pub. No.: WO2010/018686

PCT Pub. Date: Feb. 18, 2010

(65) Prior Publication Data

US 2011/0136782 A1 Jun. 9, 2011

(30) Foreign Application Priority Data

Aug. 12, 2008 (JP) ................................ 2008-207759
Jan. 14, 2009 (JP) ................................ 2009-005997

(51) Int. Cl.

| | |
|---|---|
| ***A01N 43/72*** | (2006.01) |
| ***A01P 3/00*** | (2006.01) |
| ***C07D 413/04*** | (2006.01) |
| ***C07D 417/04*** | (2006.01) |
| ***C07D 495/04*** | (2006.01) |
| ***C07D 498/04*** | (2006.01) |
| ***C07F 5/02*** | (2006.01) |
| ***C07F 5/04*** | (2006.01) |

(52) U.S. Cl.

USPC .................. 504/219; 514/211.1; 514/211.09; 540/548; 540/552

(58) Field of Classification Search

USPC ........... 504/219; 514/211.1, 211.09; 540/548, 540/552

See application file for complete search history.

(56) References Cited

FOREIGN PATENT DOCUMENTS

| | | |
|---|---|---|
| EP | 1 736 471 | 12/2006 |
| JP | 8-507049 | 7/1996 |
| JP | 2001-507341 | 6/2001 |
| WO | 94/18183 | 8/1994 |
| WO | 2005/070917 | 8/2005 |
| WO | 2006/089298 | 8/2006 |
| WO | 2007/011022 | 1/2007 |
| WO | 2007/039238 | 4/2007 |
| WO | 2008/048648 | 4/2008 |

OTHER PUBLICATIONS

Bock, Mark G., et al., "Development of 1,4-Benzodiazepine Cholecystokinin Type B Antagonists", J. Med. Chem., 1993, vol. 36, pp. 4276-4292.

Nadin, Alan, et al., "New Synthesis of 1,3-Dihydro-1,4-benzodiazepin-2(2H)-ones and 3-Amino-1,3-dihydro-1,4-benzodiazepin-2(2H)-ones: Pd-Catalyzed Cross-Coupling of Imidoyl Chlorides with Organoboronic Acids", J. Org. Chem., 2003, vol. 68, pp. 2844-2852.

Shi, Fuqiang, et al., "Method Development for a Pyridobenzodiazepine Library with Multiple Diversification Points", J. Comb. Chem., 2008, vol. 10, pp. 158-161.

European Search Report issued for EP 09806582.4, mailed Oct. 10, 2011, 17 pages.

Wakabayashi, Shigeharu, et al., "3-(Dimethylboryl)pyridine: Synthesis, Structure, and Remarkable Steric Effects in Scrambling Reactions", J. Org. Chem., 2008, vol. 73, pp. 81-87.

Suginome, Michinori, et al., "Synthesis and Helical Structure of Oligo(quinoline-2,3-diyl)s", Chemistry Letters, 2007, vol. 36, No. 8, pp. 1036-1037.

(Continued)

*Primary Examiner* — Brenda Coleman
(74) *Attorney, Agent, or Firm* — Kenyon & Kenyon LLP

(57) ABSTRACT

The present invention provides a nitrogen-containing heterocyclic compound represented by formula (I) and salt thereof (wherein, $R^1$ to $R^6$ each independently represents a hydrogen atom, unsubstituted or substituted C1-20 alkyl group and the like, $R^1$ and $R^2$, $R^3$ and $R^4$, or $R^5$ and $R^6$ may together form an unsubstituted or substituted 5- to 8-membered ring, A-B, in which A represents a carbon atom and B represents a nitrogen atom, represents the formula: C═N and the like, Y represents an oxygen atom and the like, X and X' each independently represent an unsubstituted or substituted C1-20 alkyl group and the like, m represents an integer of 0 to 2, and n represents an integer of 0 to 4), and a fungicide for agricultural and horticultural use that contains at least one of these compounds as an active ingredient thereof, demonstrates reliable effects and can be used safely. The present invention further provides a boronic acid derivative that is a production intermediate of the aforementioned compounds, and a production method thereof.

[CHEMICAL 1]

(I)

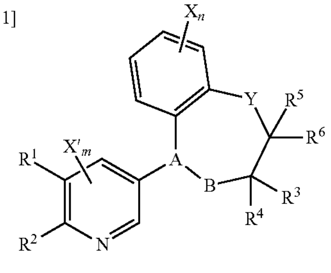

3 Claims, No Drawings

(56) References Cited

OTHER PUBLICATIONS

Yamamoto, Yasunori, et al., "Cyclic Triolborates: Air- and Water-Stable Ate Complexes of Organoboronic Acids", Angew. Chem. Int. Ed., 2008, vol. 47, pp. 928-931.
Grunewald, Gary L., et al., "Effect of Ring Size or an Additional Heteroatom on the Potency and Selectivity of Bicyclic Benzylamine-Type Inhibitors of Phenylehtanolamine *N*-Methyltransferase", J. Med. Chem., 1996, vol. 39, pp. 3539-3546.
Saeki Ken-ichi, et al., "Dual Stimulatory and Inhibitory Effects of Fluorine-Substitution on Mutagenicity: An Extension of the Enamine Epoxide Theory for Activation of the Quinoline Nucleus", Biol. Pharm. Bull., 1997, vol. 20, No. 6, pp. 646-650.
Wu, Yong-Ming, et al., "One-pot synthesis of bromodifluoroacetimidoyl halides and its Suzuki coupling reactions with aryl boronic acids", Journal of Fluorine Chemistry, 2005, vol. 126, pp. 791-795.
Fu, Renzhong, et al., "Synthesis of Novel Tricyclic Pyrimido-[4,5-*b*][1,4]benzothiazepines via Bischler-Napieralski-Type Reactions", J. Org. Chem., 2005, vol. 70, pp. 10810-10816.
Haddach, Mustapha, et al., "A New Method for the Synthesis of Ketones: The Palladium-Catalyzed Cross-Coupling of Acid Chlorides with Arylboronic Acids", Tetrahedron Letters, 1999, vol. 40, pp. 3109-3112.
Levai, Albert, et al., "Synthesis of 2,2-Dimethylbenzoxazepinones by the Schmidt Reaction of 2,2-Dimethyl-4-Chromanones", Heterocycles, 1992, vol. 34, No. 8, pp. 1523-1537.
Escale, Roger, et al, "Analogues du nor-B benzomorphane. I. Synthese des methano-3,5 tetrahydro-2,3,4,5 1*H*-benzazepines et derives", J. Heterocyclic Chem., 1984, vol. 21, pp. 1033-1040.
International Search Report (with English translation) issued during PCT/JP2009/003845, mailed Sep. 8, 2009, 8 pages.

NITROGEN-CONTAINING HETEROCYCLIC DERIVATIVE AND FUNGICIDE FOR AGRICULTURAL AND HORTICULTURAL USE

This application is a national stage entry under 35 U.S.C. §371 of PCT/JP2009/003845, filed Aug. 10, 2009. This application claims priority to Japanese Applications 2008-207759, filed on Aug. 12, 2008, and 2009-005997, filed on Jan. 14, 2009, the contents of which are incorporated herein by reference.

TECHNICAL FIELD

The present invention relates to a novel nitrogen-containing heterocyclic compound and salt thereof, and a fungicide for agricultural and horticultural use that contains at least one of these compounds as an active ingredient thereof.

The present application claims priority on Japanese Patent Application No. 2008-207759, filed in Japan on Aug. 12, 2008, and Japanese Patent Application No. 2009-005997, filed in Japan on Jan. 14, 2009, the contents of which are incorporated herein by reference.

BACKGROUND ART

In the cultivation of agricultural and horticultural crops, although numerous control agents are used against crop diseases, since their control effects are inadequate, their use has been limited due to the appearance of drug-resistant pathogens, the control agents cause chemical damage or contamination of plants, or from the viewpoint of toxicity to humans, livestock and fish or effects on the environment, few of these control agents can actually be said to be satisfactory. Thus, there is a strong need for the development of a drug that is almost free of these disadvantages and can be used safely.

In relation to the present invention, the following Patent Documents 1 and 2 disclose a quinoline derivative, which has a chemical structure that resembles that of a compound of the present invention, and a fungicide for agricultural and horticultural use that contains the quinoline derivative as an active ingredient thereof. However, there is no description of a compound of the present invention.

PRIOR ART DOCUMENTS

Patent Documents

[Patent Document 1] International Publication No. WO 2005/070917

[Patent Document 2] International Publication No. WO 2007/011022

[Patent Document 3] International Publication No. WO 2007/039238

Non-Patent Documents

[Non-Patent Document 1] Journal of Fluorine Chemistry, 126 (2005), 791-795

[Non-Patent Document 2] Tetrahedron Letters, 40 (1999), 3109-3112

[Non-Patent Document 3] Heterocycles, 34 (1992), 1523-1538

[Non-Patent Document 4] Journal of Heterocycl. Chemistry, 21 (1984), 1033-1040

[Non-Patent Document 5] J. Org. Chem., 73, 1 (2008), 81-87

[Non-Patent Document 6] Chemistry Letters, 36, 8 (2007), 1036-1037

[Non-Patent Document 7] Angew. Chem. Int. Ed., 47 (2008), 928-931

[Non-Patent Document 8] J. Med. Chem., 39 (1996), 3539-3546

[Non-Patent Document 9] Biol. Pharm. Bull., 20 (1997), 646-650

SUMMARY OF THE INVENTION

Problems to be Solved by the Invention

An object of the present invention is to provide a novel nitrogen-containing heterocyclic compound or salt thereof, and a fungicide for agricultural and horticultural use that contains at least one of these compounds as an active ingredient thereof, demonstrates reliable effects and can be used safely.

The present invention further provides a boronic acid derivative, which is a production intermediate of the aforementioned compounds, and a production method thereof.

In order to solve the aforementioned problems, the present invention provides a nitrogen-containing heterocyclic compound represented by the following formula (I), or a salt thereof (to be referred to as "the compound of the present invention"):

[CHEMICAL 1]

(I)

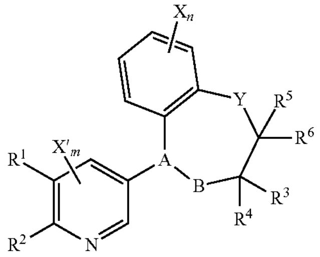

(wherein, $R^1$ and $R^2$ each independently represents a hydrogen atom, unsubstituted or substituted C1-20 alkyl group, unsubstituted or substituted C2-20 alkenyl group, unsubstituted or substituted C2-20 alkynyl group, unsubstituted or substituted C3-20 cycloalkyl group, unsubstituted or substituted C4-20 cycloalkenyl group, unsubstituted or substituted C8-20 cycloalkynyl group, unsubstituted or substituted C6-10 aryl group, unsubstituted or substituted heterocyclic group, unsubstituted or substituted C1-20 acyl group, unsubstituted or substituted (1-imino)C1-20 alkyl group, unsubstituted or substituted hydroxyl group, unsubstituted or substituted amino group, unsubstituted or substituted mercapto group, unsubstituted or substituted sulfonyl group, halogeno group, cyano group or nitro group;

$R^1$ and $R^2$ may bond together to form an unsubstituted or substituted 5- to 8-membered ring;

$R^3$ to $R^6$ each independently represents a hydrogen atom, unsubstituted or substituted C1-20 alkyl group, unsubstituted or substituted C2-20 alkenyl group, unsubstituted or substituted C2-20 alkynyl group, unsubstituted or substituted C3-20 cycloalkyl group, unsubstituted or substituted C4-20 cycloalkenyl group, unsubstituted or substituted C8-20 cycloalkynyl group, unsubstituted or substituted C6-10 aryl group, unsubstituted or substituted heterocyclic group, unsubstituted or substituted C1-20 acyl group, unsubstituted or substituted (1-imino)C1-20 alkyl group, unsubstituted or substituted hydroxyl group, unsubstituted or substituted amino group, unsubstituted or substituted mercapto group, unsubstituted or substituted sulfonyl group, halogeno group or cyano group;

a plurality of $R^3$ to $R^6$ may be selected and bond together to form an unsubstituted or substituted 3- to 8-membered ring;

$R^3$ and $R^4$, or $R^5$ and $R^6$ may bond together to form an oxo group, thioxo group or unsubstituted or substituted imino group;

A-B, in which A represents a carbon atom and B represents a nitrogen atom, represents the formula: C═N, the formula: $CR^7$—$NR^8$, the following formula (II) or the following formula (III);

[CHEMICAL 2]

(II)

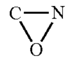

(III)

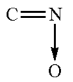

$R^7$ represents a hydrogen atom, unsubstituted or substituted C1-20 alkyl group, unsubstituted or substituted C2-20 alkenyl group, unsubstituted or substituted C2-20 alkynyl group, unsubstituted or substituted C1-20 acyl group, unsubstituted or substituted hydroxyl group, unsubstituted or substituted amino group, unsubstituted or substituted mercapto group, halogeno group or cyano group;

$R^8$ represents a hydrogen atom, unsubstituted or substituted C1-20 alkyl group, unsubstituted or substituted C2-20 alkenyl group, unsubstituted or substituted C2-20 alkynyl group, or unsubstituted or substituted C1-20 acyl group;

Y represents an oxygen atom, sulfur atom or sulfinyl group;

X and X' each independently represents an unsubstituted or substituted C1-20 alkyl group, unsubstituted or substituted C2-20 alkenyl group, unsubstituted or substituted C2-20 alkynyl group, unsubstituted or substituted C3-20 cycloalkyl group, unsubstituted or substituted C4-20 cycloalkenyl group, unsubstituted or substituted C8-20 cycloalkynyl group, unsubstituted or substituted C6-10 aryl group, unsubstituted or substituted heterocyclic group, unsubstituted or substituted C1-20 acyl group, unsubstituted or substituted (1-imino)C1-20 alkyl group, unsubstituted or substituted hydroxyl group, unsubstituted or substituted amino group, unsubstituted or substituted mercapto group, unsubstituted or substituted sulfonyl group, halogeno group, cyano group or nitro group;

m represents an integer of 0 to 2; and, n represents an integer of 0 to 4).

In the nitrogen-containing heterocyclic compound or salt thereof of the present invention, a compound represented by the following formula (IV) or salt thereof in which $R^1$ and $R^2$ bond together to form a ring is preferable:

[CHEMICAL 3]

(IV)

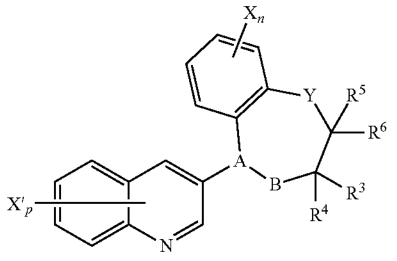

(wherein, X, X', n, $R^3$ to $R^6$, A-B and Y are the same as previously defined, and p represents an integer of 0 to 6).

In addition, among compounds represented by formula (IV), a compound represented by the following formula (IX) or salt thereof is more preferable:

[CHEMICAL 4]

(IX)

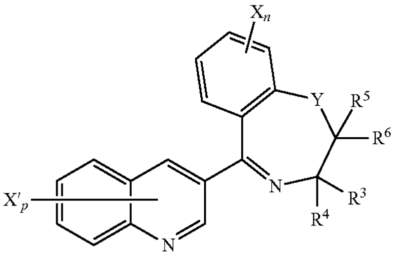

(wherein, X, X', n, p, $R^3$ to $R^6$ and Y are the same as previously defined).

The present invention further provides a production method of a production intermediate used to produce a nitrogen-containing heterocyclic compound represented by the aforementioned formula (IV) or formula (IX).

Namely, a C1-6 alkyl magnesium hydride and a C1-6 alkyl lithium are reacted followed by reacting with a compound represented by the following formula (V):

[CHEMICAL 5]

(V)

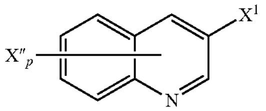

(wherein, X" each independently represents an unsubstituted or substituted C1-20 alkyl group, unsubstituted or substituted C2-20 alkenyl group, unsubstituted or substituted C2-20 alkynyl group, unsubstituted or substituted C3-20 cycloalkyl group, unsubstituted or substituted C4-20 cycloalkenyl group, unsubstituted or substituted C8-20 cycloalkynyl group, unsubstituted or substituted C6-10 aryl group, unsubstituted or substituted heterocyclic group, unsubstituted or substituted hydroxyl group, unsubstituted or substituted amino group, unsubstituted or substituted mercapto group, fluorine atom, chlorine atom or nitro group;

q represents an integer of 0 to 6; and, $X^1$ represents a bromine atom or iodine atom), followed by reacting with a compound represented by the formula (VI): $B(OR^{12})_3$ (wherein, $R^{12}$ each independently represents a C1-6 alkyl group)

to produce a boronic acid derivative represented by the following formula (VII):

[CHEMICAL 6]

(VII)

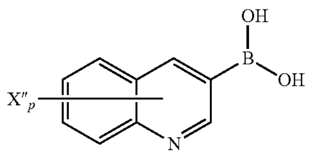

(wherein, X" and q are the same as previously defined).

The present invention further provides a boronic acid derivative represented by the following formula (VIII) that is a production intermediate used to produce a nitrogen-containing heterocyclic compound represented by the aforementioned formula (IV) or formula (IX):

[CHEMICAL 7]

(VIII)

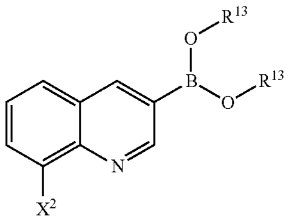

(wherein, $X^2$ represents a fluorine atom or chlorine atom, $R^{13}$ each independently represents a hydrogen atom or C1-20 alkyl group, and $R^{13}$ may mutually bond together to form a 5- to 8-membered ring).

The present invention further provides a boronic acid derivative represented by the following formula (X) that is a production intermediate used to produce a nitrogen-containing heterocyclic compound represented by the aforementioned formula (IV) or formula (IX):

[CHEMICAL 8]

(X)

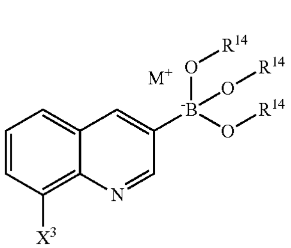

(wherein, $X^3$ represents a hydrogen atom, fluorine atom or chlorine atom, $R^{14}$ each independently represents a C1-20 alkyl group, $R^{14}$ may mutually bond to form a 5- to 8-membered ring, and M represents an alkaline metal).

In addition, among compounds represented by formula (X), a compound represented by the following formula (X') is preferable:

[CHEMICAL 9]

(X')

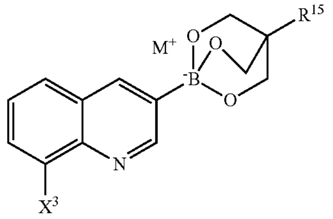

(wherein, $X^3$ and M are the same as previously defined, and $R^{15}$ represents a C1-20 alkyl group).

The present invention further provides a fungicide for agricultural and horticultural use that contains at least one of the nitrogen-containing heterocyclic compounds represented by the aforementioned formula (I), formula (IV) or formula (IX), or salt thereof.

Effects of the Invention

The nitrogen-containing heterocyclic compound or salt thereof of the present invention is a novel compound, and is useful as an active ingredient of a fungicide for agricultural and horticultural use that demonstrates reliable effects and can be used safely.

The fungicide for agricultural and horticultural use of the present invention is an agent that has superior control effects, does not cause chemical damage to plants, and has little toxicity on humans, livestock or fish and little effect on the environment.

In addition, the boronic acid derivative of the present invention is useful as an intermediate of a nitrogen-containing heterocyclic compound and the like of the present invention.

MODE FOR CARRYING OUT THE INVENTION

The following provides a detailed explanation of the present invention by dividing into sections of: 1) nitrogen-containing heterocyclic compound represented by formula (I), formula (IV) or formula (IX), or salt thereof, and intermediate thereof and 2) fungicide for agricultural and horticultural use.

1) Nitrogen-Containing Heterocyclic Compound Represented by Formula (I), Formula (IV) or Formula (IX), or Salt Thereof, and Intermediate Thereof (Nitrogen-Containing Heterocyclic Compound Represented by Formula (I), or Salt Thereof)

The present invention relates to a nitrogen-containing heterocyclic compound represented by the aforementioned formula (I), or a salt thereof. Hydrates, various types of solvates, crystalline polymorphs and the like are included in the compound of the present invention or salt thereof. Moreover, stereoisomers based on an asymmetric carbon atom or double bond and the like as well as mixtures thereof are also included in the compound of the present invention.

In formula (I), the "C1-20 alkyl group" of the "unsubstituted or substituted C1-20 alkyl group" of $R^1$ to $R^8$, X and X' refers to a linear or branched alkyl group having 1 to 20 carbon atoms. Examples include a methyl group, ethyl group, n-propyl group, n-butyl group, n-pentyl group, n-hexyl group, n-heptyl group, n-octyl group, nonyl group, n-decyl group, dodecyl group, tridecyl group, tetradecyl group, pentadecyl group, hexadecyl group, heptadecyl group, octadecyl group, nonadecyl group, icosyl group, i-propyl group, i-butyl group, s-butyl group, t-butyl group, isopentyl group, neopentyl group, 2-methylbutyl group, 2,2-dimethylpropyl group, isohexyl group, isononyl group, 2-ethyloctyl group, 3-ethyloctyl group, 2,3-dimethyloctyl group, 4-propyloctyl group, 4-ethyldecyl group, 6-ethyldodecyl group, 3,5-dimethyldecyl group, 2,5-dimethyldecyl group, 6-propylnonyl group, 4-butyloctyl group, 2,4,6,8-tetramethyldecyl group, 2,2-diethyldecyl group, 2,5-diethyldecyl group, 4-butyldecyl group and 2,4,6,8-tetraethyldecyl group. Among these, C1-6 alkyl groups are preferable.

The "C2-20 alkenyl group" of the "unsubstituted or substituted C2-20 alkenyl group" of $R^1$ to $R^8$, X and X' refers to a linear or branched alkenyl group having 2 to 20 carbon atoms and having a carbon-carbon double bond at one or more locations of an alkyl group. Examples include a vinyl group, 1-propenyl group, allyl group, 1-butenyl group, 2-butenyl group, 3-butenyl group, 1-pentenyl group, 2-pentenyl group, 3-pentenyl group, 4-pentenyl group, 1-hexenyl group, 2-hexenyl group, 3-hexenyl group, 4-hexenyl group, 5-hexenyl group, 1-heptenyl group, 6-heptenyl group, 1-octenyl group, 7-octenyl group, 1-decenyl group, 9-decenyl group, 1-dodecenyl group, 4-dodecenyl group, 1-octadecenyl group, 1-methyl-2-propenyl group, 2-methyl-2-propenyl group, 1-methyl-2-butenyl group, 2-methyl-2-butenyl group and 2-ethyl-1-octadecenyl group. Among these, C2-6 alkenyl groups are preferable.

The "C2-20 alkynyl group" of the "unsubstituted or substituted C2-20 alkynyl group" of $R^1$ to $R^8$, X and X' refers to a linear or branched alkynyl group having 2 to 20 carbon atoms and having a carbon-carbon triple bond at one or more locations of an alkyl group. Examples include an ethynyl group, 1-propynyl group, propargyl group, 1-butynyl group, 2-butynyl group, 3-butynyl group, 1-pentynyl group, 2-pentynyl group, 3-pentynyl group, 4-pentynyl group, 1-hexynyl group, dodecynyl group, butadecynyl group, heptadecynyl group, 1-methyl-2-propynyl group, 2-methyl-3-butynyl group, 1-methyl-2-butynyl group, 2-methyl-3-pentynyl group, 1,1-dimethyl-2-butynyl group and 4-ethylhexadecynyl group. Among these, C2-6 alkynyl groups are preferable.

The "C3-20 cycloalkyl group" of the "unsubstituted or substituted C3-20 cycloalkyl group" of $R^1$ to $R^6$, X and X' refers to an alkyl group having 3 to 20 carbon atoms having a cyclic moiety. Examples include a cyclopropyl group, cyclobutyl group, cyclopentyl group, cyclohexyl group, cycloheptyl group, cyclooctyl group and norbornyl group. Among these, C3-6 cycloalkyl groups are preferable.

The "C4-20 cycloalkenyl group" of the "unsubstituted or substituted C4-20 cycloalkenyl group" of $R^1$ to $R^6$, X and X' refers to an alkenyl group having 4 to 20 carbon atoms having acyclic moiety. Examples include a 1-cyclobutenyl group, 1-cyclopentenyl group, 3-cyclopentenyl group, 1-cyclohexenyl group, 3-cyclohexenyl group, 3-cycloheptenyl group and 4-cyclooctenyl group. Among these C4-8 cycloalkenyl groups are preferable.

The "C8-20 cycloalkynyl group" of the "unsubstituted or substituted C8-20 cycloalkynyl group" of $R^1$ to $R^6$, X and X' refers to an alkynyl group having 8 to 20 carbon atoms having a cyclic moiety. Examples include a 5-cyclooctynyl group, 6-cyclodecynyl group and 7-cyclododecynyl group. Among these C8-12 cycloalkynyl groups are preferable.

The "C6-10 aryl group" of the "unsubstituted or substituted C6-10 aryl group" of $R^1$ to $R^6$, X and X' refers to a monocyclic or polycyclic aryl group having 6 to 10 carbon atoms. Here, in the case of polycyclic aryl groups, partially saturated groups are also included in addition to completely unsaturated groups. Examples include a phenyl group, naphthyl group, azurenyl group, indenyl group, indanyl group and tetralinyl group. Among these, a phenyl group is preferable.

The "heterocyclic group" of the "unsubstituted or substituted heterocyclic group" of $R^1$ to $R^6$, X and X' refers to an aromatic heterocycle, saturated heterocycle, unsaturated heterocycle or 9- to 10-membered condensed heterocycle, in which these heterocycles are condensed with a benzene ring, that contain 1 to 4 hetero atoms other than carbon atoms selected from the group consisting of a nitrogen atom, oxygen atom and sulfur atom as atoms that compose the ring. Examples include an aziridin-1-yl group, aziridin-2-yl group, epoxy group; tetrahydrofuran-2-yl group, tetrahydrofuran-3-yl group, pyrrolidin-1-yl group, pyrrolidin-2-yl group, pyrrolidin-3-yl group, pyrrol-1-yl group, pyrrol-2-yl group, pyrrol-3-yl group, furan-2-yl group, furan-3-yl group, thiophen-2-yl group, thiophen-3-yl group, imidazol-1-yl group, imidazol-2-yl group, imidazol-4-yl group, imidazol-5-yl group, pyrazol-1-yl group, pyrazol-3-yl group, pyrazol-4-yl group, pyrazol-5-yl group, oxazol-2-yl group, oxazol-4-yl group, oxazol-5-yl group, thiazol-2-yl group, thiazol-4-yl group, thiazol-5-yl group, isoxazol-3-yl group, isoxazol-4-yl group, isoxazol-5-yl group, isothiazol-3-yl group, isothiazol-4-yl group, isothiazol-5-yl group, 1,2,3-triazol-1-yl group, 1,2,3-triazol-4-yl group, 1,2,3-triazol-5-yl group, 1,2,4-triazol-1-yl group, 1,2,4-triazol-3-yl group, 1,2,4-triazol-5-yl group, 1,3,4-oxadiazol-2-yl group, 1,2,4-oxadizol-3-yl group, 1,3,4-thiadiazol-2-yl group, 1,2,4-thiadiazol-3-yl group, tetrazol-1-yl group, tetrazol-2-yl group; pyridin-2-yl group, pyridin-3-yl group, pyridin-4-yl group, pyrazin-2-yl group, pyrimidin-2-yl group, pyrimidin-4-yl group, pyrimidin-5-yl group, pyridazin-3-yl group, pyridazin-4-yl group, triazinyl group; indol-1-yl group, indol-2-yl group, indol-3-yl group, indol-4-yl group, indol-5-yl group, indol-6-yl group, indol-7-yl group, benzofuran-2-yl group, benzofuran-3-yl group, benzofuran-4-yl group, benzofuran-5-yl group, benzofuran-6-yl group, benzofuran-7-yl group, benzothiophen-2-yl group, benzothiophen-3-yl group, benzothiophen-4-yl group, benzothiophen-5-yl group, benzothiophen-6-yl group, benzothiophen-7-yl group, isoindol-1-yl group, isoindol-2-yl group, isoindol-4-yl group, isoindol-5-yl group, isoindol-6-yl group, isoindol-7-yl group, isobenzofuran-1-yl group, isobenzofuran-4-yl group, isobenzofuran-5-yl group, isobenzofuran-6-yl group, isobenzofuran-7-yl group, benzoimidazol-1-yl group, benzoimidazol-2-yl group, benzoimidazol-4-yl group, benzoimidazol-5-yl group, benzoxazol-2-yl group, benzoxazol-4-yl group, benzoxazol-5-yl group, benzothiazol-2-yl group, benzothiazol-4-yl group, benzothiazol-5-yl group; chromen-2-yl group, chromen-3-yl group, chromen-4-yl group, chromen-5-yl group, chromen-6-yl group, chromen-7-yl group, chromen-8-yl group, quinolin-2-yl group, quinolin-3-yl group, quinolin-4-yl group, quinolin-5-yl group, quinolin-6-yl group, quinolin-7-yl group, quinolin-8-yl group, isoquinolin-1-yl group, isoquinolin-3-yl group, isoquinolin-4-yl group, isoquinolin-5-yl group, isoquinolin-6-yl group, isoquinolin-7-yl group, isoquinolin-8-yl group; piperidin-1-yl group, piperidin-2-yl group, piperidin-3-yl group, piperidin-4-yl group, piperazin-1-yl group, piperazin-2-yl group, piperazin-3-yl group, morpholin-2-yl group, morpholin-3-yl group, morpholin-4-yl group, 1,3-benzodioxazol-4-yl group, 1,3-benzodioxazol-5-yl group, 1,4-benzodioxan-5-yl group, 1,4-benzodioxan-6-yl group, 3,4-dihydro-2H-1,5-benzodioxepin-6-yl group, 3,4-dihydro-2H-1,5-benzodioxepin-7-yl group, 2,3-dihydrobenzofuran-4-yl group, 2,3-dihydrobenzofuran-5-yl group, 2,3-dihydrobenzofuran-6-yl group, and 2,3-dihydrobenzofuran-7-yl group.

Among these, 5- to 10-membered heterocyclic groups are preferable.

The "C1-20 acyl group" of the "unsubstituted or substituted C1-20 acyl group" of $R^1$ to $R^8$, X and X' refers to a group in which a hydrogen atom, linear or branched C1-19 alkyl group, linear or branched C2-19 alkenyl group, linear or branched C2-19 alkynyl group, monocyclic or polycyclic C6-19 aryl group or 5- to 7-membered heterocyclic group that that contains 1 to 4 hetero atoms other than carbon atoms selected from the group consisting of a nitrogen atom, oxygen atom and sulfur atom as atoms that compose the ring, is bonded to a carbonyl group.

Examples include alkylcarbonyl groups such as a formyl group, acetyl group, propionyl group, n-propylcarbonyl group, n-butylcarbonyl group, pentanoyl group, valeryl group, octanoyl group, nonanoyl group, decanoyl group, undecanoyl group, dodecanoyl group, tridecanoyl group, tetradecanoyl group, pentadecanoyl group, hexadecanoyl group, heptadecanoyl group, octadecanoyl group, nonadecanoyl group, icosanoyl group, henaicosanoyl group, i-propylcarbonyl group, i-butylcarbonyl group, pivaloyl group, isovaleryl group, 3-methylnonanoyl group, 8-methylnonanoyl group, 3-ethyloctanoyl group, 3,7-dimethyloctanoyl group, 1-methylpentadecanoyl group, 14-methylpentadecanoyl group, 13,13-dimethyltetradecanoyl group, 15-methylhexadecanoyl group or 1-methylheptadecanoyl group; alkenylcarbonyl groups such as an acryloyl group or methacryloyl group; alkynylcarbonyl groups such as a propioloyl group; arylcarbonyl groups such as a benzoyl group, naphthylcarbonyl group, biphenylcarbonyl group or anthranylcarbonyl group; and, heterocyclic carbonyl groups such as a 2-pyridylcarbonyl group or thienylcarbonyl group. Among these, C1-7 acyl groups are preferable.

The "(1-imino)C1-20 alkyl group" of the "unsubstituted or substituted (1-imino)C1-20 alkyl group" of $R^1$ to $R^6$, X and X' refers to a group in which a linear or branched C1-19 alkyl group is bonded to an iminomethyl group. Examples include an iminomethyl group, (1-imino)ethyl group, (1-imino)propyl group, (1-imino)butyl group, (1-imino)pentyl group, (1-imino)hexyl group, (1-imino)heptyl group, (1-imino)octylimino group, (1-imino)isobutyl group, (1-imino)isopentyl group and (1-imino)neopentyl group. Among these, (1-imino)C1-6 alkyl groups are preferable.

Examples of the "halogeno group" of $R^1$ to $R^7$, X and X' include a fluorine atom, chlorine atom, bromine atom and iodine atom.

In addition to the examples described above, $R^1$ and $R^2$ may bond together to form an unsubstituted or substituted 5- to 8-membered ring. Examples of 5- to 8-membered rings include aromatic hydrocarbon rings, aromatic heterocycles, aliphatic hydrocarbon rings and unsaturated heterocycles, and aromatic hydrocarbon rings are preferable.

More specifically, examples of aromatic hydrocarbon rings include a benzene ring, and examples of aromatic heterocycles include a furan ring, thiophene ring, pyrrole ring, pyridine ring, pyrazine ring, pyrimidine ring, pyridazine ring, imidazole ring, pyrazole ring, thiazole ring, oxazole ring and isoxazole ring.

Examples of aliphatic hydrocarbon rings include cycloalkene rings such as a cyclopentene ring, cyclohexene ring, cycloheptene ring or cyclooctene ring.

Examples of unsaturated heterocycles include a dihydro-2H-pyran ring, dihydro-2H-thiopyran ring and tetrahydropyridine ring.

Among these, a benzene ring is preferable. Namely, the compound of the present invention is preferably that which forms a quinoline ring by condensation of a pyridine ring and benzene ring in formula (I).

In addition to the examples described above, a plurality of $R^3$ to $R^6$ may be selected and together form an unsubstituted or substituted 3- to 8-membered ring. Examples of 3- to 8-membered rings include aliphatic hydrocarbon rings, aromatic hydrocarbon rings, aromatic heterocycles and unsaturated heterocycles.

More specifically, examples of aliphatic hydrocarbon rings include cycloalkane rings such as a cyclopropane ring, cyclopentane ring, cyclohexane ring, cycloheptane ring or cyclooctane ring.

Examples of aromatic hydrocarbon rings include a benzene ring, and examples of aromatic heterocycles include a furan ring, thiophene ring, pyrrole ring, pyridine ring, pyrazine ring, pyrimidine ring, pyridazine ring, imidazole ring, pyrazole ring, thiazole ring, oxazole ring and isoxazole ring.

Examples of unsaturated heterocycles include a dihydro-2H-pyran ring, dihydro-2H-thiopyran ring and tetrahydropyridine ring.

Although various groups can be selected for use as $R^3$ to $R^6$ in the compound of the present invention, C1-6 alkyl groups are preferable.

Although various groups can be selected for use as X and X' in the compound of the present invention, halogeno groups are preferable.

In the formula, A-B, in which A represents a carbon atom and B represents a nitrogen atom, represents the formula: C═N, the formula: $CR^7$—$NR^6$, the following formula (II) or the following formula (III).

[CHEMICAL 10]

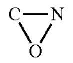

(II)

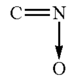

(III)

$R^7$ represents a hydrogen atom, unsubstituted or substituted C1-20 alkyl group, unsubstituted or substituted C2-20 alkenyl group, unsubstituted or substituted C2-20 alkynyl group, unsubstituted or substituted C1-20 acyl group, unsubstituted or substituted hydroxyl group, unsubstituted or substituted amino group, unsubstituted or substituted mercapto group, halogeno group or cyano group.

$R^8$ represents a hydrogen atom, unsubstituted or substituted C1-20 alkyl group, unsubstituted or substituted C2-20 alkenyl group, unsubstituted or substituted C2-20 alkynyl group, or unsubstituted or substituted C1-20 acyl group.

A-B is preferably represented by the formula: C═N.

In the formula, Y represents an oxygen atom, sulfur atom or sulfinyl group, and preferably represents an oxygen atom.

There are no particular limitations on salts of the compound of the present invention provided it is an agriculturally and horticulturally allowable salt. Examples include salts of inorganic acids such as hydrochloric acid or sulfuric acid; salts of organic acids such as acetic acid or lactic acid; salts of alkaline metals such as lithium, sodium or potassium; salts of alkaline earth metals such as calcium or magnesium; salts of transition metals such as iron or copper; and, salts of organic bases such as ammonia, triethylamine, tributylamine, pyridine or hydrazine.

(Explanation of "Substituted" and "Unsubstituted or Substituted")

In the present description, the terms "substituted" or "unsubstituted or substituted" refers that a hydrogen atom of any of the aforementioned "groups" is substituted with a "substituent", or is unsubstituted or substituted with a "substituent". Although examples of "substituents" include each of the aforementioned "groups", these "substituents" may also be "substituents" substituted with still "other groups". Examples of "other groups" include each of the aforementioned "groups".

The following indicates examples of each of the aforementioned "groups" being substituted by any of the aforementioned "groups".

In the "unsubstituted or substituted C1-20 alkyl group" of $R^1$ to $R^8$, X and X', examples of the "C1-20 alkyl group" substituted by the "unsubstituted or substituted C3-20 cycloalkyl group" include a cyclopropylmethyl group, 2-cyclopropylethyl group, cyclopentylmethyl group, 2-cyclohexylethyl group and 2-cyclooctylethyl group. Among these, C4-10 cycloalkyl C1-6 alkyl groups are preferable.

In the "unsubstituted or substituted C1-20 alkyl group" of $R^1$ to $R^8$, X and X', examples of the "C1-20 alkyl group" substituted by the "unsubstituted or substituted C4-20 cycloalkenyl group" include a cyclopentenylmethyl group, 3-cyclopentatenylmethyl group, 3-cyclohexenylmethyl group and 2-(3-cyclohexenyl)ethyl group. Among these, C4-8 cycloalkenyl C1-6 alkyl groups are preferable.

In the "unsubstituted or substituted C1-20 alkyl group" of $R^1$ to $R^8$, X and X', examples of the "C1-20 alkyl group" substituted by the "unsubstituted or substituted C8-20 cycloalkynyl group" include a 5-cyclooctynylmethyl group. Among these, C9-13 cycloalkynyl C1-6 alkyl groups are preferable.

In the "unsubstituted or substituted C1-20 alkyl group" of $R^1$ to $R^8$, X and X', examples of the "C1-20 alkyl group" substituted by the "halogeno group" include a fluoromethyl group, chloromethyl group, bromomethyl group, difluoromethyl group, dichloromethyl group, dibromomethyl group, trifluoromethyl group, trichloromethyl group, tribromomethyl group, 2,2,2-trifluoroethyl group, 2,2,2-trichloroethyl group, pentafluoroethyl group, 4-fluorobutyl group, 4-chlorobutyl group, 3,3,3-trifluoropropyl group, 2,2,2-trifluoro-1-trifluoromethylethyl group, perfluorohexyl group, perchlorohexyl group, perfluorooctyl group, perchlorooctyl group, 2,4,6-trichlorohexyl group, perfluorodecyl group, 2,2,4,4,6,6-hexachlorooctyl group and 2,2,4,4,6,6-hexachloro-3-propyloctyl group. Among these, C1-6 alkyl groups in which 1 to 3 halogen atoms are substituted therein (to be referred to as "C1-6 haloalkyl groups") are preferable.

In the "unsubstituted or substituted C1-20 alkyl group" of $R^1$ to $R^8$, X and X', examples of the "C1-20 alkyl group" substituted by the "unsubstituted or substituted C6-10 aryl group" include a benzyl group, phenethyl group, 3-phenylpropyl group, 1-naphthylmethyl group and 2-naphthylmethyl group. Among these, C6-10 aryl C1-6 alkyl groups are preferable.

In the "unsubstituted or substituted C1-20 alkyl group" of $R^1$ to $R^8$, X and X', examples of the "C1-20 alkyl group" substituted by the "unsubstituted or substituted heterocyclic group" include a 2-pyridylmethyl group, 3-pyridylmethyl group, 4-pyridylmethyl group, 2-(2-pyridyl)ethyl group, 2-(3-pyridyl)ethyl group, 2-(4-pyridyl)ethyl group, 3-(2-pyridyl)propyl group, 3-(3-pyridyl)propyl group, 3-(4-pyridyl)propyl group, 2-pyrazinylmethyl group, 3-pyrazinylmethyl group, 2-(2-pyrazinyl)ethyl group, 2-(3-pyrazinyl)ethyl group, 3-(2-pyrazinyl)propyl group, 3-(3-pyrazinyl)propyl group, 2-pyrimidylmethyl group, 4-pyrimidylmethyl group, 2-(2-pyrimidyl)ethyl group, 2-(4-pyrimidyl)ethyl group, 3-(2-pyrimidyl)propyl group, 3-(4-pyrimidyl)propyl group, 2-furylmethyl group, 3-furylmethyl group, 2-(2-furyl)ethyl group, 2-(3-furyl)ethyl group, 3-(2-furyl)propyl group and 3-(3-furyl)propyl group. Among these, 5- to 10-membered heterocyclic C1-6 alkyl groups are preferable.

In the "unsubstituted or substituted C1-20 alkyl group" of $R^1$ to $R^8$, X and X', examples of the "C1-20 alkyl group" substituted by the "hydroxyl group" include a hydroxymethyl group, hydroxyethyl group and hydroxypropyl group. Among these, hydroxy C1-6 alkyl groups are preferable.

Moreover, among "unsubstituted or substituted C1-20 alkyl groups substituted with a hydroxyl group", or in other words, "unsubstituted or substituted hydroxy C1-20 alkyl groups", examples of the "hydroxy C1-20 alkyl group" substituted by the "unsubstituted or substituted C1-20 alkyl group" include a methoxymethyl group, ethoxymethyl group, methoxyethyl group, ethoxyethyl group, methoxy-n-propyl group, ethoxymethyl group, ethoxyethyl group, n-propoxymethyl group, i-propoxyethyl group, s-butoxymethyl group, t-butoxyethyl group and 2,2-dimethoxyethyl group. Among these, C1-6 alkoxy C1-6 alkyl groups are preferable.

In addition, in the "unsubstituted or substituted hydroxy C1-20 alkyl group", examples of the "hydroxy C1-20 alkyl group" substituted by the "unsubstituted or substituted C1-20 acyl group" include a formyloxymethyl group, acetoxymethyl group, 2-acetoxyethyl group, propionyloxymethyl group and propionyloxyethyl group. Among these, C2-7 acyloxy C1-6 alkyl groups are preferable.

In the "unsubstituted or substituted C3-20 cycloalkyl group" of $R^1$ to $R^6$, X and X', examples of the "C3-20 cycloalkyl group" substituted by the "unsubstituted or substituted C1-20 alkyl group" include a 2,3,3-trimethylcyclobutyl group, 4,4,6,6-tetramethylcyclohexyl group and 1,3-dibutylcyclohexyl group. Among these, C4-10 cycloalkyl groups substituted with 1 to 3 C1-6 alkyl groups are preferable.

In the "unsubstituted or substituted C4-20 cycloalkenyl group" of $R^1$ to $R^6$, X and X', examples of the "C4-20 cycloalkenyl group" substituted by the "unsubstituted or substituted C1-20 alkyl group" include a 2-methyl-3-cyclohexenyl group and 3,4-dimethyl-3-cyclohexenyl group. Among these, C5-9 cycloalkenyl groups substituted with 1 to 3 C1-6 alkyl groups are preferable.

In the "unsubstituted or substituted C8-20 cycloalkynyl group" of $R^1$ to $R^6$, X and X', examples of the "C8-20 cycloalkynyl group" substituted by the "unsubstituted or substituted C1-20 alkyl group" include a 2,3-diethyl-4-cyclodecynyl group. Among these, C9-12 cycloalkynyl groups substituted with 1 to 3 C1-6 alkyl groups are preferable.

In the "unsubstituted or substituted C2-20 alkenyl group" of $R^1$ to $R^8$, X and X', examples of the "C2-20 alkenyl group" substituted by the "halogeno group" include a 3-chloro-2-propenyl group, 4-chloro-2-butenyl group, 4,4-dichloro-3-butenyl group, 4,4-difluoro-3-butenyl group, 3,3-dichloro-2-propenyl group, 2,3-dichloro-2-propenyl group, 3,3-difluoro-2-propenyl group and 2,4,6-trichloro-2-hexenyl group. Among these, C2-6 alkenyl groups substituted with 1 to 3 halogen atoms are preferable.

In the "unsubstituted or substituted C2-20 alkynyl group" of $R^1$ to $R^8$, X and X', examples of the "C2-20 alkynyl group" substituted by the "halogeno group" include a 3-chloro-1-propynyl group, 3-chloro-1-butynyl group, 3-bromo-1-butynyl group, 3-bromo-2-propynyl group, 3-iodo-2-propynyl group, 3-bromo-1-hexynyl group, 4,4,6,6-tetrafluoro-1-dodecynyl group, 5,5-dichloro-2-methyl-3-pentynyl group and 4-chloro-1,1-dimethyl-2-butynyl group. Among these, C2-6 alkynyl groups substituted with 1 to 3 halogen atoms are preferable.

In the "unsubstituted or substituted hydroxyl group" in $R^1$ to $R^7$, X and X', examples of the "hydroxyl group" substituted by the "unsubstituted or substituted C1-20 alkyl group, or in other words, an "unsubstituted or substituted C1-20 alkoxy group", include a methoxy group, ethoxy group, n-propoxy group, n-butoxy group, n-pentyloxy group, n-hexyloxy group, decyloxy group, dodecyloxy group, lauryloxy group, i-propoxy group, i-butoxy group, s-butoxy group, t-butoxy group, 1-ethylpropoxy group, isohexyloxy group, 4-methylpentoxy group, 3-methylpentoxy group, 2-methylpentoxy group, 1-methylpentoxy group, 3,3-dimethylbutoxy group, 2,2-dimethylbutoxy group, 1,1-dimethylbutoxy group, 1,2-dimethylbutoxy group, 1,3-dimethylbutyoxy group, 2,3-dimethylbutoxy group, 1-ethylbutoxy group, 2-ethylbutoxy group and 2-ethyldecyloxy group, and examples of the "alkoxy group" substituted by the "unsubstituted or substituted C3-20 cycloalkyl group" or the "unsubstituted or substituted C6-10 aryl group" include a cyclopropylmethyloxy group, 2-cyclopentylethyloxy group and benzyloxy group. Among these, C1-7 alkoxy groups are preferable.

In addition, examples of a "group" in which the aforementioned "alkoxy group" is substituted by the "halogen group" include a chloromethoxy group, dichloromethoxy group, trichloromethoxy group, trifluoromethoxy group, 1-fluoroethoxy group, 1,1-difluoroethoxy group, 2,2,2-trifluoroethoxy group and pentafluoroethoxy group. Among these, C1-6 alkoxy groups substituted with 1 to 3 halogen atoms (which may be referred to as "C1-6 haloalkoxy groups") are preferable.

In the "unsubstituted or substituted hydroxyl group" of $R^1$ to $R^7$, X and X', examples of the "hydroxyl group" substituted by the "unsubstituted or substituted C2-20 alkenyl group", or in other words, an "unsubstituted or substituted C2-20 alkenyloxy group", include a vinyloxy group, 1-propenyloxy group, 2-propenyloxy group, 1-butenyloxy group, 2-butenyloxy group, 3-butenyloxy group, 1-pentenyloxy group, 2-pentenyloxy group, 3-pentenyloxy group, 4-pentenyloxy group, 1-hexenyloxy group, 2-hexenyloxy group, 3-hexenyloxy group, 4-hexenyloxy group, 5-hexenyloxy group, 1-heptenyloxy group, 6-heptenyloxy group, 1-octenyloxy group, 7-octenyloxy group, 1-decenyloxy group, 9-decenyloxy group, 1-dodecenyloxy group, 4-dodecenyloxy group, 1-octadecenyloxy group, 1-methyl-2-propenyloxy group, 2-methyl-2-propenyloxy group, 1-methyl-2-butenyloxy group, 2-methyl-2-butenyloxy group and 2-ethyl-1-octadecenyloxy group. Among these, C2-6 alkenyloxy groups are preferable.

In a "substituted hydroxyl group" of $R^1$ to $R^7$, X and X', examples of the "hydroxyl group" substituted by the "unsubstituted or substituted C2-20 alkynyl group", or in other words, a "C2-20 alkynyloxy group", include an ethynyloxy group, propynyloxy group, propargyloxy group, 1-butynyloxy group, 2-butynyloxy group, 3-butynyloxy group, 1-pentynyloxy group, 2-pentynyloxy group, 3-pentynyloxy group, 4-pentynyloxy group, 1-hexynyloxy group, dodecynyloxy group, butadecynyloxy group, heptadecynyloxy group, 1-methyl-2-propynyloxy group, 2-methyl-3-butynyloxy group, 1-methyl-2-butynyloxy group, 2-methyl-3-pentynyloxy group, 1,1-dimethyl-2-butynyloxy group and 4-ethylhexadecynyloxy group. Among these, C2-6 alkynyloxy groups are preferable.

In the "substituted hydroxyl group" of $R^1$ to $R^7$, X and X', examples of the "hydroxyl group" substituted by the "unsubstituted or substituted C3-20 cycloalkyl group", or in other words, a "C3-20 cycloalkoxy group", include a cyclopropyloxy group, cyclobutyloxy group, cyclopentyloxy group, cyclohexyloxy group, cycloheptyloxy group and cyclooctyloxy group, and examples of the cycloalkoxy group substituted by the "unsubstituted or substituted C1-20 alkyl group" include a 2-methylcyclopropyloxy group, 2-ethylcyclopropyloxy group, 2,3,3-trimethylcyclobutyloxy group, 2-methylcyclopentyloxy group, 2-ethylcyclohexyloxy group, 2-ethylcyclooctyloxy group, 4,4,6,6-tetramethylcyclohexyloxy group and 1,3-dibutylcyclohexyloxy group. Among these, C3-6 cycloalkoxy groups are preferable.

In the "substituted hydroxyl group" of $R^1$ to $R^7$, X and X', the "hydroxyl group" substituted by the "unsubstituted or substituted C6-10 aryl group", or in other words, an "unsubstituted or substituted C6-10 aryloxy group", include a phenyloxy group, naphthyloxy group, azurenyloxy group, indenyloxy group, indanyloxy group and tetralinyloxy group. Among these, C6-10 aryloxy groups are preferable.

In the "substituted hydroxyl group" of $R^1$ to $R^7$, X and X', examples of the "hydroxyl group" substituted by the "unsubstituted or substituted C1-20 acyl group", or in other words an "unsubstituted or substituted C1-20 acyloxy group", include an acetyloxy group, propionyloxy group, n-propylcarbonyloxy group, i-propylcarbonyloxy group, n-butylcarbonyloxy group, i-butylcarbonyloxy group, pentanoyloxy group and pivaloyloxy group. Among these, C1-7 acyloxy groups are preferable.

In the "unsubstituted or substituted C1-20 acyl group" of $R^1$ to $R^8$, X and X', examples of the "C1-20 acyl group" substituted by the "halogeno group" include a monofluoroacetyl group, monochloroacetyl group, monobromoacetyl group, difluoroacetyl group, dichloroacetyl group, dibromoacetyl group, trifluoroacetyl group, trichloroacetyl group, tribromoacetyl group, 3,3,3-trifluoropropionyl group, 3,3,3-trichloropropionyl group and 2,2,3,3,3-pentafluoropropinoyl group. Among these, C1-6 acyl groups substituted with 1 to 3 halogen atoms are preferable.

In the "unsubstituted or substituted C1-20 acyl group" of $R^1$ to $R^8$, X and X', examples of the "C1-20 acyl group" substituted by the "unsubstituted or substituted C2-20 alkenyl group", "unsubstituted or substituted C2-20 alkynyl group", "unsubstituted or substituted C6-10 aryl group" or "unsubstituted or substituted heterocyclic group" include a 3-allylphenylcarbonyl group, 3-ethynyl-phenylcarbonyl group, benzylcarbonyl group, phenethylcarbonyl group and 2-pyridylmethylcarbonyl group.

In the "unsubstituted or substituted C1-20 acyl group" of $R^1$ to $R^8$, X and X', an example of a "group" in which an "unsubstituted or substituted C1 acyl group" is substituted by the "hydroxyl group" is a "carboxyl group".

In the "unsubstituted or substituted C1-20 acyl group" of $R^1$ to $R^8$, X and X', an example of a "group" in which the "C1 acyl group" is substituted by the "substituted hydroxyl group" is a "substituted carboxyl group". In this "substituted carboxyl group", examples of the "carboxyl group" substituted by the "unsubstituted or substituted C1-20 alkyl group" include a methoxycarbonyl group, ethoxycarbonyl group, n-propoxycarbonyl group, i-propoxycarbonyl group, n-butoxycarbonyl group, i-butoxycarbonyl group, t-butoxycarbonyl group, n-pentyloxycarbonyl group, n-hexyloxycarbonyl group, decyloxycarbonyl group, dodecyloxycarbonyl group, 2-ethyldecyloxycarbonyl group and lauryloxycarbonyl group. Moreover, examples of an "alkyl-substituted carboxyl group" substituted by the "unsubstituted or substituted C3-20 cycloalkyl group" or "unsubstituted or substituted C6-10 aryl group" include a cyclopropylmethyloxycarbonyl group, 2-cyclopentylethyloxycarbonyl group and benzyloxycarbonyl group. Among these, C1-7 alkoxycarbonyl groups are preferable.

In the "unsubstituted or substituted (1-imino)C1-20 alkyl group" of $R^1$ to $R^6$, X and X', an example of a "group" in which a hydrogen atom bonded to the nitrogen atom of the iminomethyl group is substituted by the "hydroxyl group" is an "unsubstituted or substituted (1-hydroxyimino)C1-20 alkyl group". Examples thereof include a hydroxyiminomethyl group, (1-hydroxyimino)ethyl group, (1-hydroxyimino)propyl group and (1-hydroxyimino)butyl group. Among these, (1-hydroxyimino)C1-6 alkyl groups are preferable.

In addition, in the "unsubstituted or substituted (1-hydroxyimino)C1-20 alkyl group", examples of a "group" in which a hydrogen atom of the hydroxyl group is substituted by the "unsubstituted or substituted C1-20 alkyl group" include a methoxyiminomethyl group, (1-ethoxyimino)methyl group and (1-ethoxyimino)ethyl group. Among these, (1-(C1-6 alkoxy)imino)C1-6 alkyl groups are preferable.

In the "unsubstituted or substituted amino group" of $R^1$ to $R^7$, X and X', examples of the "amino group" substituted by the "unsubstituted or substituted C1-20 alkyl group" include a methylamino group, ethylamino group, dimethylamino group and diethylamino group. Among these, mono-C1-6 alkylamino groups or di-C1-6 alkylamino groups are preferable.

In addition, examples of a "group" in which two hydrogen atoms of the amino group are substituted on the same carbon atom as the "unsubstituted or substituted C1-20 alkyl group" include a methylideneamino group and ethylideneamino group. Among these, mono-C1-6 alkylideneamino groups are preferable.

In addition, other examples in addition to those described above include monoarylamino groups such as a phenylamino group or 4-methylphenylamino group (and preferably, mono-C6-10 arylamino groups); diarylamino groups such as a di-1-naphthylamino group (and preferably, di-C6-10 arylamino groups); and acylamino groups such as an acetylamino group or benzoylamino group (and preferably, C1-6 acylamino groups).

In the "unsubstituted or substituted C1-20 acyl group" of $R^1$ to $R^8$, X and X', an example of a "group" in which the "C1 acyl group" is substituted by a "substituted amino group" is a "substituted carbamoyl group". In this "substituted carbamoyl group", examples of a "carbamoyl group" substituted by the "unsubstituted or substituted C1-20 alkyl group" include a methylcarbamoyl group, ethylcarbamoyl group, dimethylcarbamoyl group and diethylcarbamoyl group. Among these, mono-C1-6 alkylcarbamoyl groups or di-C1-6 alkylcarbamoyl groups are preferable.

In addition, other examples in addition to those described above include carbamoyl groups; monoarylcarbamoyl groups such as a phenylcarbamoyl group or 4-methylphenylcarbamoyl group (and preferably, mono-C6-10 arylcarbamoyl groups); and acylcarbamoyl groups such as an acetylcarbamoyl group or benzoylcarbamoyl group (and preferably, C1-6 acylcarbamoyl groups).

In the "unsubstituted or substituted mercapto group" of $R^1$ to $R^7$, X and X', examples of a "mercapto group" substituted by the "unsubstituted or substituted C1-20 alkyl group" include a methylthio group and ethylthio group. Among these, C1-6 alkylthio groups are preferable. In addition, other examples in addition to those described above include arylthio groups such as a phenylthio group or 4-methylphenylthio group (and preferably, C6-10 arylthio groups), and acylthio groups such as an acetylthio group or benzoylthio group (and preferably, C1-6 acylthio groups).

In the "substituted sulfonyl group" of $R^1$ to $R^6$, X and X', examples of a "sulfonyl group" substituted by the "unsubstituted or substituted C1-20 alkyl group" include a methylsulfonyl group, ethylsulfonyl group, n-propylsulfonyl group, isopropylsulfonyl group, n-butylsulfonyl group, isobutylsulfonyl group, sec-butylsulfonyl group, tert-butylsulfonyl group, n-pentylsulfonyl group, isopentylsulfonyl group, neopentylsulfonyl group, 1-ethylpropylsulfonyl group, n-hexylsulfonyl group and isohexylsulfonyl group. Among these, C1-6 alkylsulfonyl groups are preferable.

In addition, other examples in addition to those described above include haloalkylsulfonyl groups such as a trifluoromethylsulfonyl group (and preferably, C1-6 haloalkylsulfonyl groups); arylsulfonyl groups such as a phenylsulfonyl group or 4-methylphenylsulfonyl group (and preferably, C6-10 arylsulfonyl groups); sulfo groups; alkoxysulfonyl groups such as a methoxysulfonyl group or ethoxysulfonyl group (and preferably, C1-6 alkoxysulfonyl groups); sulfamoyl groups; sulfamoyl groups such as an N-methylsulfamoyl group, N-ethylsulfamoyl group, N,N-dimethylsulfamoyl group or N,N-diethylsulfamoyl group (and preferably, mono-C1-6 alkylsulfamoyl groups or di-C1-6 alkylsulfamoyl groups); and monoarylsulfamoyl groups such as a phenylsulfamoyl group or 4-methylphenylsulfamoyl group (and preferably, mono-C6-10 arylsulfamoyl groups).

In the "unsubstituted or substituted imino group" of $R^3$ and $R^4$, or $R^5$ and $R^6$, examples of an "imino group" substituted by the "unsubstituted or substituted C6-10 alkyl group" include a methylimino group and benzylimino group, and examples of an "imino group" substituted by the "unsubstituted or substituted hydroxyl group" include a hydroxyimino group and ethoxyimino group.

Other examples of "substituents" in addition to those described above in the "substituted" and "unsubstituted or substituted" of $R^1$ to $R^8$, X and X' include groups represented by —Si $(R^{20})(R^{21})(R^{22})$ such as —Si $(Me)_3$, —$SiPh_3$, —Si $(cPr)_3$ or —$Si(Me)_2$(t-Bu) (wherein, t-Bu represents a tertiary butyl group, and the same shall apply hereinafter).

The aforementioned $R^{20}$, $R^{21}$ and $R^{22}$ each independently represents a C1-6 alkyl group or phenyl group. Examples of C1-6 alkyl groups are the same as those indicated for $R^1$ to $R^8$, X and X'.

(Nitrogen-Containing Heterocyclic Compound Represented by Formula (IV))

The compound represented by the aforementioned formula (I) is preferably a compound represented by formula (IV) in which $R^1$ and $R^2$ in formula (I) are bonded together:

[CHEMICAL 11]

(IV)

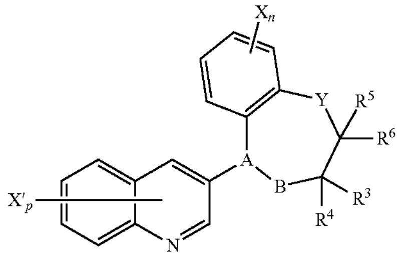

(wherein, X, X', n, $R^3$ to $R^6$, A-B and Y are the same as previously defined, and p represents an integer of 0 to 6).

(Nitrogen-Containing Heterocyclic Compound Represented by Formula (IX))

The compound represented by the aforementioned formula (IV) is more preferably a compound represented by formula (IX), wherein A-B in formula (IV) is the formula C═N:

[CHEMICAL 12]

(IX)

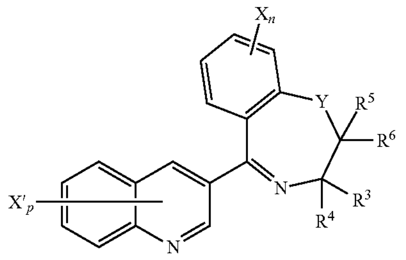

(wherein, X, X', n, p, $R^3$ to $R^6$ and Y are the same as previously defined).

(Examples of Compounds)

Specific examples of compounds represented by formulas (I), (IV) and (IX) include the compounds listed in the following Tables 1 to 17. Furthermore, in the tables, Me represents a methyl group, Et represents an ethyl group, n-Pr represents an n-propyl group, i-Pr represents an i-propyl group, c-Pr represents a cyclopropyl group, t-Bu represents a t-butyl group, Ac represents an acetyl group, Bn represents a benzyl group and Ph represents a phenyl group.

TABLE 1

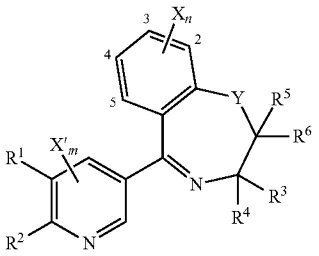

| Compound No. | $R^1$ | $R^2$ | $R^3$ | $R^4$ | $R^5$ | $R^6$ | X'm | Xn | Y |
|---|---|---|---|---|---|---|---|---|---|
| A1-1 | $—(CH_2)_4—$ | | H | H | H | H | — | — | O |
| A1-2 | $—(CH_2)_4—$ | | Me | Me | H | H | — | — | O |
| A1-3 | $—(CH_2)_4—$ | | H | H | Me | Me | — | — | O |
| A1-4 | $—(CH_2)_4—$ | | Me | Me | Me | Me | — | — | O |
| A1-5 | $—(CH_2)_4—$ | | Me | Me | Cl | Cl | — | — | O |
| A1-6 | $—(CH_2)_4—$ | | Cl | Cl | Cl | Cl | — | — | O |
| A1-7 | $—(CH_2)_4—$ | | $—(CH_2)_5—$ | | H | H | — | — | O |
| A1-8 | $—(CH_2)_4—$ | | H | H | $—(CH_2)_5—$ | | — | — | O |
| A1-9 | $—(CH_2)_4—$ | | $—(CH_2)_4—$ | | H | H | — | — | O |
| A1-10 | H | H | H | H | H | H | — | — | O |
| A1-11 | Me | Me | H | H | H | H | — | — | O |
| A1-12 | Et | Et | H | H | H | H | — | — | O |
| A1-13 | MeO | MeO | H | H | H | H | — | — | O |
| A1-14 | $NO_2$ | $NO_2$ | H | H | H | H | — | — | O |
| A1-15 | CN | CN | H | H | H | H | — | — | O |
| A1-16 | $NH_2$ | $NH_2$ | H | H | H | H | — | — | O |
| A1-17 | Cl | Cl | H | H | H | H | — | — | O |
| A1-18 | $CF_3$ | $CF_3$ | H | H | H | H | — | — | O |
| A1-19 | $—(CH_2)_4—$ | | Me | Me | Me | Me | — | 2-Cl | O |
| A1-20 | —CH═CH—S— | | H | H | Me | Me | — | 2-Cl | O |
| A1-21 | Me | Me | H | H | H | H | — | 2-Cl | O |
| A1-22 | $—(CH_2)_3—$ | | Me | Me | Me | Me | — | 2-Cl | O |
| A1-23 | —CH═CH—CH═N— | | H | H | Me | Me | — | 2-Cl | O |

TABLE 2

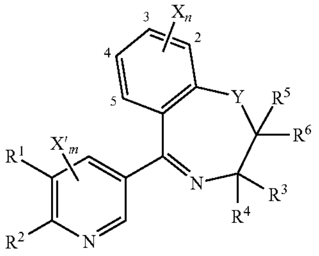

| Compound No. | $R^1$ | $R^2$ | $R^3$ | $R^4$ | $R^5$ | $R^6$ | X'm | Xn | Y |
|---|---|---|---|---|---|---|---|---|---|
| A2-1 | $—(CH_2)_4—$ | | H | H | H | H | — | — | S |
| A2-2 | $—(CH_2)_4—$ | | Me | Me | H | H | — | — | S |
| A2-3 | $—(CH_2)_4—$ | | H | H | Me | Me | — | — | S |
| A2-4 | $—(CH_2)_4—$ | | Me | Me | Me | Me | — | — | S |
| A2-5 | $—(CH_2)_4—$ | | Cl | Cl | Cl | Cl | — | — | S |
| A2-6 | Me | Me | H | H | H | H | — | — | S |
| A2-7 | $—(CH_2)_4—$ | | $—(CH_2)_5—$ | | H | H | — | — | S |
| A2-8 | $—(CH_2)_4—$ | | $—(CH_2)_4—$ | | H | H | — | — | S |

TABLE 3

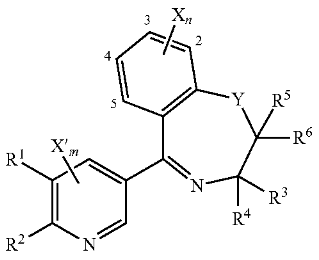

| Compound No. | $R^1$ | $R^2$ | $R^3$ | $R^4$ | $R^5$ | $R^6$ | X'm | Xn | Y |
|---|---|---|---|---|---|---|---|---|---|
| A3-1 | $—(CH_2)_4—$ | | H | H | O | | — | — | O |
| A3-2 | $—(CH_2)_4—$ | | Me | Me | O | | — | — | O |
| A3-3 | $—(CH_2)_4—$ | | Cl | Cl | O | | — | — | O |
| A3-4 | Me | Me | H | H | O | | — | — | O |
| A3-5 | $—(CH_2)_4—$ | | H | H | NH | | — | — | O |
| A3-6 | $—(CH_2)_4—$ | | H | H | N—OH | | — | — | O |
| A3-7 | $—(CH_2)_4—$ | | H | H | O | | — | — | S |
| A3-8 | $—(CH_2)_4—$ | | Me | Me | O | | — | — | S |
| A3-9 | $—(CH_2)_4—$ | | Cl | Cl | O | | — | — | S |
| A3-10 | Me | Me | H | H | O | | — | — | S |

TABLE 5

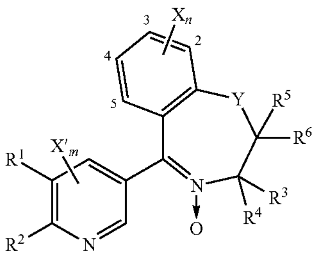

| Compound No. | $R^1$ | $R^2$ | $R^3$ | $R^4$ | $R^5$ | $R^6$ | X'm | Xn | Y |
|---|---|---|---|---|---|---|---|---|---|
| A5-1 | $—(CH_2)_4—$ | | H | H | H | H | — | — | O |
| A5-2 | $—(CH_2)_4—$ | | Me | Me | H | H | — | — | O |
| A5-3 | $—(CH_2)_4—$ | | H | H | Me | Me | — | — | O |
| A5-4 | $—(CH_2)_4—$ | | Me | Me | Me | Me | — | — | O |
| A5-5 | $—(CH_2)_4—$ | | Me | Me | Cl | Cl | — | — | O |
| A5-6 | $—(CH_2)_4—$ | | Cl | Cl | Cl | Cl | — | — | O |
| A5-7 | $—(CH_2)_4—$ | | $—(CH_2)_5—$ | | H | H | — | — | O |
| A5-8 | $—(CH_2)_4—$ | | H | H | $—(CH_2)_5—$ | | — | — | O |
| A5-9 | $—(CH_2)_4—$ | | $—(CH_2)_4—$ | | H | H | — | — | O |
| A5-10 | H | H | H | H | H | H | — | — | O |
| A5-11 | Me | Me | H | H | H | H | — | — | O |

TABLE 4

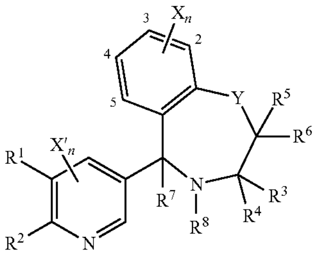

| Compound No. | $R^1$ | $R^2$ | $R^3$ | $R^4$ | $R^5$ | $R^6$ | $R^7$ | $R^8$ | X'm | Xn | Y |
|---|---|---|---|---|---|---|---|---|---|---|---|
| A4-1 | $—(CH_2)_4—$ | | H | H | H | H | H | H | — | — | O |
| A4-2 | $—(CH_2)_4—$ | | Me | Me | H | H | H | H | — | — | O |
| A4-3 | $—(CH_2)_4—$ | | H | H | Me | Me | H | H | — | — | O |
| A4-4 | $—(CH_2)_4—$ | | Me | Me | Me | Me | H | H | — | — | O |
| A4-5 | $—(CH_2)_4—$ | | Me | Me | Cl | Cl | H | H | — | — | O |
| A4-6 | $—(CH_2)_4—$ | | Cl | Cl | Cl | Cl | H | H | — | — | O |
| A4-7 | $—(CH_2)_4—$ | | $—(CH_2)_5—$ | | H | H | H | H | — | — | O |
| A4-8 | $—(CH_2)_4—$ | | H | H | $—(CH_2)_5—$ | | H | H | — | — | O |
| A4-9 | $—(CH_2)_4—$ | | $—(CH_2)_4—$ | | H | H | H | H | — | — | O |
| A4-10 | H | H | H | H | H | H | H | H | — | — | O |
| A4-11 | Me | Me | H | H | H | H | H | H | — | — | O |
| A4-12 | Et | Et | H | H | H | H | H | H | — | — | O |
| A4-13 | MeO | MeO | H | H | H | H | H | H | — | — | O |
| A4-14 | $NO_2$ | $NO_2$ | H | H | H | H | H | H | — | — | O |
| A4-15 | CN | CN | H | H | H | H | H | H | — | — | O |
| A4-16 | $NH_2$ | $NH_2$ | H | H | H | H | H | H | — | — | O |
| A4-17 | Cl | Cl | H | H | H | H | H | H | — | — | O |
| A4-18 | $CF_3$ | $CF_3$ | H | H | H | H | H | H | — | — | O |
| A4-19 | $—(CH_2)_4—$ | | H | H | H | H | H | Ac | — | — | O |
| A4-20 | $—(CH_2)_4—$ | | Me | Me | H | H | H | Ac | — | — | O |
| A4-21 | $—(CH_2)_4—$ | | Me | Me | Me | Me | H | Ac | — | — | O |
| A4-22 | $—(CH_2)_4—$ | | Cl | Cl | Cl | Cl | H | Ac | — | — | O |
| A4-23 | $—(CH_2)_4—$ | | $—(CH_2)_5—$ | | H | H | H | Ac | — | — | O |
| A4-24 | $—(CH_2)_4—$ | | $—(CH_2)_4—$ | | H | H | H | Ac | — | — | O |
| A4-25 | H | H | H | H | H | H | H | Ac | — | — | O |
| A4-26 | Me | Me | H | H | H | H | H | Ac | — | — | O |

TABLE 5-continued

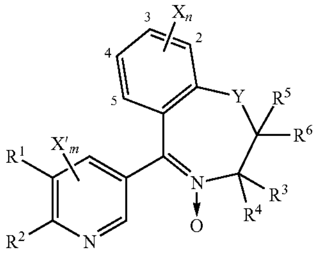

| Compound No. | $R^1$ | $R^2$ | $R^3$ | $R^4$ | $R^5$ | $R^6$ | X'm | Xn | Y |
|---|---|---|---|---|---|---|---|---|---|
| A5-12 | MeO | MeO | H | H | H | H | — | — | O |
| A5-13 | Cl | Cl | H | H | H | H | — | — | O |
| A5-14 | $—(CH_2)_4—$ | | H | H | H | H | — | — | S |
| A5-15 | $—(CH_2)_4—$ | | Me | Me | H | H | — | — | S |
| A5-16 | $—(CH_2)_4—$ | | Me | Me | Me | Me | — | — | S |
| A5-17 | $—(CH_2)_4—$ | | Cl | Cl | Cl | Cl | — | — | S |
| A5-18 | $—(CH_2)_4—$ | | $—(CH_2)_5—$ | | H | H | — | — | S |

TABLE 6

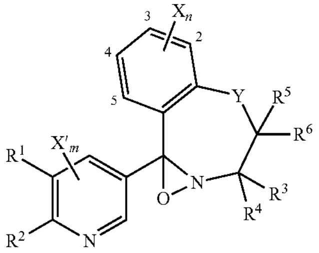

| Compound No. | $R^1$ | $R^2$ | $R^3$ | $R^4$ | $R^5$ | $R^6$ | X'm | Xn | Y |
|---|---|---|---|---|---|---|---|---|---|
| A6-1 | $—(CH_2)_4—$ | | H | H | H | H | — | — | O |
| A6-2 | $—(CH_2)_4—$ | | Me | Me | H | H | — | — | O |
| A6-3 | $—(CH_2)_4—$ | | H | H | Me | Me | — | — | O |
| A6-4 | $—(CH_2)_4—$ | | Me | Me | Me | Me | — | — | O |
| A6-5 | $—(CH_2)_4—$ | | Me | Me | Cl | Cl | — | — | O |
| A6-6 | $—(CH_2)_4—$ | | Cl | Cl | Cl | Cl | — | — | O |
| A6-7 | $—(CH_2)_4—$ | | $—(CH_2)_5—$ | | H | H | — | — | O |
| A6-8 | $—(CH_2)_4—$ | | H | H | $—(CH_2)_5—$ | | — | — | O |
| A6-9 | $—(CH_2)_4—$ | | $—(CH_2)_4—$ | | H | H | — | — | O |
| A6-10 | H | H | H | H | H | H | — | — | O |
| A6-11 | Me | Me | H | H | H | H | — | — | O |
| A6-12 | MeO | MeO | H | H | H | H | — | — | O |
| A6-13 | Cl | Cl | H | H | H | H | — | — | O |
| A6-14 | $—(CH_2)_4—$ | | H | H | H | H | — | — | S |
| A6-15 | $—(CH_2)_4—$ | | Me | Me | H | H | — | — | S |
| A6-16 | $—(CH_2)_4—$ | | Me | Me | Me | Me | — | — | S |
| A6-17 | $—(CH_2)_4—$ | | Cl | Cl | Cl | Cl | — | — | S |
| A6-18 | $—(CH_2)_4—$ | | $—(CH_2)_5—$ | | H | H | — | — | S |

TABLE 7

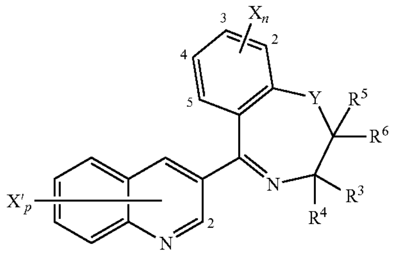

| Compound No. | $R^3$ | $R^4$ | $R^5$ | $R^6$ | X'p | Xn | Y |
|---|---|---|---|---|---|---|---|
| B1-1 | H | H | H | H | — | — | O |
| B1-2 | Me | H | H | H | — | — | O |
| B1-3 | Me | Me | H | H | — | — | O |
| B1-4 | Et | Me | H | H | — | — | O |
| B1-5 | n-Pr | Me | H | H | — | — | O |
| B1-6 | $CH_2═CH$ | Me | H | H | — | — | O |
| B1-7 | Cl | Me | H | H | — | — | O |
| B1-8 | Meo | Me | H | H | — | — | O |
| B1-9 | H | H | Me | Me | — | — | O |
| B1-10 | $CF_3$ | Me | H | H | — | — | O |
| B1-11 | Me | Me | Me | Me | — | — | O |
| B1-12 | Me | Me | Cl | Cl | — | — | O |
| B1-13 | Cl | Cl | H | H | — | — | O |
| B1-14 | Cl | Cl | Cl | Cl | — | — | O |
| B1-15 | H | H | Cl | Cl | — | — | O |
| B1-16 | H | H | H | H | 5-F | — | O |
| B1-17 | H | H | H | H | 6-F | — | O |
| B1-18 | H | H | H | H | 7-Cl | — | O |
| B1-19 | H | H | H | H | 8-Cl | — | O |
| B1-20 | H | H | H | H | 5-Me | — | O |
| B1-21 | H | H | H | H | 6-Me | — | O |
| B1-22 | H | H | H | H | 6-MeO | — | O |
| B1-23 | H | H | H | H | 7-MeO | — | O |
| B1-24 | H | H | H | H | 5-OH | — | O |
| B1-25 | H | H | H | H | 6-OH | — | O |
| B1-26 | $—(CH_2)_5—$ | | H | H | — | — | O |
| B1-27 | H | H | $—(CH_2)_5—$ | | — | — | O |
| B1-28 | $—(CH_2)_4—$ | | H | H | — | — | O |
| B1-29 | Me | H | Cl | Me | — | — | O |
| B1-30 | H | H | Cl | Me | — | 2-F | O |

TABLE 8

| Compound No. | $R^3$ | $R^4$ | $R^5$ | $R^6$ | X'p | Xn | Y |
|---|---|---|---|---|---|---|---|
| B1-31 | H | H | Me | Et | — | — | O |
| B1-32 | H | H | Et | Et | — | — | O |
| B1-33 | H | H | Me | Me | — | 2-Me | O |
| B1-34 | H | H | Me | Me | — | 2-Cl | O |
| B1-35 | H | H | Me | i-Pr | — | — | O |
| B1-36 | H | H | Me | Me | — | 2-F | O |
| B1-37 | H | H | Me | Me | 8-F | — | O |
| B1-38 | H | H | Me | Me | 8-F | 2-F | O |
| B1-39 | H | H | Me | Me | 8-F | 2-Cl | O |
| B1-40 | H | H | Me | Me | 8-Me | 2-Cl | O |
| B1-41 | H | H | Me | Me | 8-Cl | 2-Cl | O |
| B1-42 | H | Me | Me | Me | — | — | O |
| B1-43 | Me | Me | Me | Me | — | 2-F | O |
| B1-44 | H | H | Me | Me | — | $2-CF_3$ | O |
| B1-45 | Me | Me | Me | Me | 8-F | 2-F | O |
| B1-46 | H | H | Me | Me | 8-Cl | — | O |
| B1-47 | H | H | Me | Et | 8-F | — | O |
| B1-48 | H | H | Me | Et | 8-F | 2-Cl | O |
| B1-49 | H | H | Me | Et | 8-F | 2-F | O |
| B1-50 | Me | Me | Me | Me | 8-F | — | O |
| B1-51 | H | H | Me | $CF_3$ | — | — | O |
| B1-52 | H | H | Me | Ph | — | — | O |
| B1-53 | H | H | Me | 4-F-Bn | — | — | O |
| B1-54 | H | H | Me | Me | — | 2-CN | O |
| B1-55 | H | H | Me | Me | — | 2-MeO | O |

TABLE 8-continued

| Compound No. | $R^3$ | $R^4$ | $R^5$ | $R^6$ | X'p | Xn | Y |
|---|---|---|---|---|---|---|---|
| B1-56 | H | H | Me | $CF_3$ | 8-F | — | O |
| B1-57 | H | H | Me | Me | 5-Cl | 2-Cl | O |
| B1-58 | H | H | Me | Me | 5-Me | 2-Cl | O |
| B1-59 | H | H | Me | Me | 6-Cl | 2-Cl | O |
| B1-60 | H | H | Me | Me | 6-Me | 2-Cl | O |

TABLE 9

| Compound No. | $R^3$ | $R^4$ | $R^5$ | $R^6$ | X'p | Xn | Y |
|---|---|---|---|---|---|---|---|
| B1-61 | H | H | Me | Me | 7-Cl | 2-Cl | O |
| B1-62 | H | H | Me | Me | 7-Me | 2-Cl | O |
| B1-63 | H | H | Me | Me | 6,8-$F_2$ | 2-Cl | O |
| B1-64 | H | H | Me | Me | — | 2-Cl | O |
| B1-65 | H | H | Me | Me | — | 2-Cl | O |
| B1-66 | H | H | Me | Me | 8-F | 2-F | O |
| B1-67 | H | H | Me | Me | 8-F | 2-Cl | O |
| B1-68 | H | H | Me | n-Pr | — | — | O |
| B1-69 | H | H | Me | CN | — | — | O |
| B1-70 | H | H | Me | c-Pr | — | — | O |
| B1-71 | H | H | Me | $CF_3CH_2$ | — | — | O |
| B1-72 | H | H | —$(CH_2)_3$— | | — | — | O |
| B1-73 | H | H | Me | Me | — | 2-Ph | O |
| B1-74 | H | H | Me | Me | — | 2-Bn | O |
| B1-75 | H | H | Me | Me | — | 2-($CH_2$═CH) | O |
| B1-76 | H | H | Me | Me | — | 3-Cl | O |
| B1-77 | H | H | Me | Me | — | 4-Cl | O |
| B1-78 | H | H | Me | Me | — | 5-Cl | O |
| B1-79 | H | H | Me | Me | 8-F | 2-Me | O |
| B1-80 | Ph | Me | H | H | — | — | O |
| B1-81 | 4-F-Bn | Me | H | H | — | — | O |
| B1-82 | H | H | Me | Me | — | 2-OPh | O |
| B1-83 | | | Ph | | — | — | O |
| B1-84 | | ═O | H | H | — | — | O |
| B1-85 | H | H | Me | Me | — | 3-F | O |
| B1-86 | H | H | H | H | — | 5-F | O |

Among the above compounds, compounds B1-64 and B1-67 are HCl salts, while compounds B1-65 and B1-66 are TFA salts (trifluoroacetic acid salts).

TABLE 10

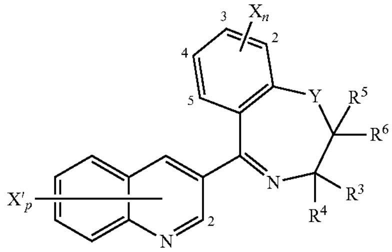

| Compound No. | $R^3$ | $R^4$ | $R^5$ | $R^6$ | X'p | Xn | Y |
|---|---|---|---|---|---|---|---|
| B2-1 | H | H | H | H | — | — | S |
| B2-2 | Me | H | H | H | — | — | S |
| B2-3 | Me | Me | H | H | — | — | S |
| B2-4 | Et | Me | H | H | — | — | S |
| B2-5 | n-Pr | Me | H | H | — | — | S |
| B2-6 | H | H | Me | Me | — | — | S |
| B2-7 | Me | Me | Me | Me | — | — | S |
| B2-8 | Cl | Cl | Cl | Cl | — | — | S |
| B2-9 | H | H | H | H | 5-F | — | S |
| B2-10 | H | H | H | H | 6-F | — | S |
| B2-11 | —$(CH_2)_5$— | | H | H | — | — | S |

TABLE 10-continued

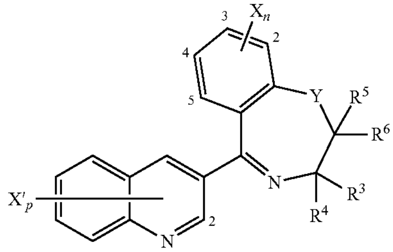

| Compound No. | $R^3$ | $R^4$ | $R^5$ | $R^6$ | X'p | Xn | Y |
|---|---|---|---|---|---|---|---|
| B2-12 | —$(CH_2)_4$— | | H | H | — | — | S |
| B2-13 | H | H | Me | Me | 8-F | — | S |
| B2-14 | H | H | Me | Me | — | 2-F | S |
| B2-15 | H | H | Me | Me | 8-F | 2-F | S |
| B2-16 | H | H | Me | Me | — | — | SO |

TABLE 11

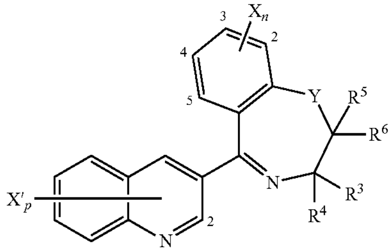

| Compound No. | $R^3$ | $R^4$ | $R^5$ | $R^6$ | X'p | Xn | Y |
|---|---|---|---|---|---|---|---|
| B3-1 | H | H | O | | — | — | O |
| B3-2 | Me | Me | O | | — | — | O |
| B3-3 | Cl | Cl | O | | — | — | O |
| B3-4 | H | H | O | | 5-F | — | O |
| B3-5 | H | H | O | | 6-F | — | O |
| B3-6 | H | H | NH | | — | — | O |
| B3-7 | H | H | N—OH | | — | — | O |
| B3-8 | H | H | O | | — | — | S |
| B3-9 | Me | Me | O | | — | — | S |
| B3-10 | Cl | Cl | O | | — | — | S |
| B3-11 | H | H | O | | 5-F | — | S |
| B3-12 | H | H | O | | 6-F | — | S |

TABLE 12

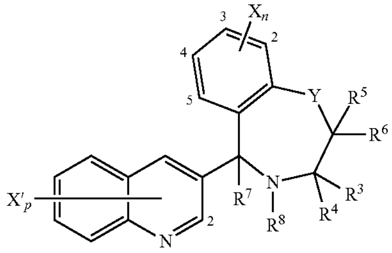

| Compound No. | $R^3$ | $R^4$ | $R^5$ | $R^6$ | $R^7$ | $R^8$ | X'p | Xn | Y |
|---|---|---|---|---|---|---|---|---|---|
| B4-1 | H | H | H | H | H | H | — | — | O |
| B4-2 | Me | H | H | H | H | H | — | — | O |
| B4-3 | Me | Me | H | H | H | H | — | — | O |
| B4-4 | Et | Me | H | H | H | H | — | — | O |
| B4-5 | n-Pr | Me | H | H | H | H | — | — | O |

TABLE 12-continued

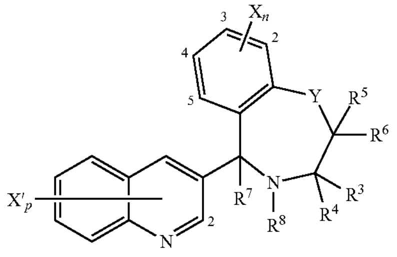

| Compound No. | $R^3$ | $R^4$ | $R^5$ | $R^6$ | $R^7$ | $R^8$ | X'p | Xn | Y |
|---|---|---|---|---|---|---|---|---|---|
| B4-6 | $CH_2$=CH | Me | H | H | H | H | — | — | O |
| B4-7 | Cl | Me | H | H | H | H | — | — | O |
| B4-8 | MeO | Me | H | H | H | H | — | — | O |
| B4-9 | H | H | Me | Me | H | H | — | — | O |
| B4-10 | Me | H | Me | Me | H | H | — | — | O |
| B4-11 | Me | Me | Me | Me | H | H | — | — | O |
| B4-12 | Me | Me | Cl | Cl | H | H | — | — | O |
| B4-13 | Cl | Cl | H | H | H | H | — | — | O |
| B4-14 | Cl | Cl | Cl | Cl | H | H | — | — | O |
| B4-15 | H | H | Cl | Cl | H | H | — | — | O |
| B4-16 | H | H | H | H | H | H | 5-F | — | O |
| B4-17 | H | H | H | H | H | H | 6-F | — | O |
| B4-18 | H | H | H | H | H | H | 7-Cl | — | O |
| B4-19 | H | H | H | H | H | H | 8-Cl | — | O |
| B4-20 | H | H | H | H | H | H | 5-Me | — | O |
| B4-21 | H | H | H | H | H | H | 6-Me | — | O |
| B4-22 | H | H | H | H | H | H | 6-MeO | — | O |
| B4-23 | H | H | H | H | H | H | 7-MeO | — | O |
| B4-24 | H | H | H | H | H | H | 5-OH | — | O |
| B4-25 | H | H | H | H | H | H | 6-OH | — | O |
| B4-26 | —$(CH_2)_5$— | | H | H | H | H | — | — | O |
| B4-27 | H | H | —$(CH_2)_5$— | | H | H | — | — | O |
| B4-28 | —$(CH_2)_4$— | | H | H | H | H | — | — | O |
| B4-29 | H | H | H | H | H | Ac | — | — | O |
| B4-30 | Me | Me | H | H | H | Ac | — | — | O |

TABLE 13

| Compound No. | $R^3$ | $R^4$ | $R^5$ | $R^6$ | $R^7$ | $R^8$ | X'p | Xn | Y |
|---|---|---|---|---|---|---|---|---|---|
| B4-31 | H | H | Me | Me | H | Ac | — | — | O |
| B4-32 | Me | Me | Me | Me | H | Ac | — | — | O |
| B4-33 | Cl | Cl | H | H | H | Ac | — | — | O |
| B4-34 | Cl | Cl | Cl | Cl | H | Ac | — | — | O |
| B4-35 | H | H | Cl | Cl | H | Ac | — | — | O |
| B4-36 | H | H | H | H | H | Ac | 5-F | — | O |
| B4-37 | H | H | H | H | H | Ac | 6-F | — | O |
| B4-38 | —$(CH_2)_5$— | | H | H | H | Ac | — | — | O |
| B4-39 | H | H | —$(CH_2)_5$— | | H | Ac | — | — | O |
| B4-40 | H | H | H | H | H | $CO_2Me$ | — | — | O |
| B4-41 | Me | Me | H | H | H | $CO_2Me$ | — | — | O |
| B4-42 | Me | Me | Me | Me | H | $CO_2Me$ | — | — | O |
| B4-43 | Cl | Cl | Cl | Cl | H | $CO_2Me$ | — | — | O |
| B4-44 | —$(CH_2)_5$— | | H | H | H | $CO_2Me$ | — | — | O |
| B4-45 | H | H | —$(CH_2)_5$— | | H | $CO_2Me$ | — | — | O |
| B4-46 | | O | Me | Me | H | H | — | — | O |
| B4-47 | H | H | Me | Me | H | H | 8-F | 2-F | O |
| B4-48 | H | H | Me | Me | H | Et | 8-F | 2-F | O |
| B4-49 | H | H | Me | Me | H | H | 8-F | 2-Cl | O |
| B4-50 | H | H | Me | Me | H | Bn | 8-F | 2-Cl | O |
| B4-51 | H | H | Me | Me | H | CHO | 8-F | 2-F | O |
| B4-52 | H | H | Me | Me | H | Ac | 8-F | 2-F | O |
| B4-53 | | =O | Me | Me | H | H | — | — | O |

TABLE 14

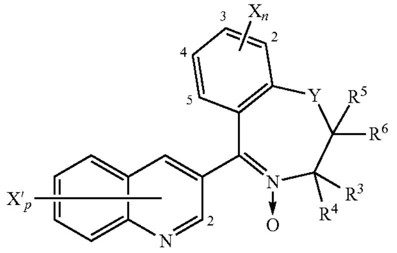

| Compound No. | $R^3$ | $R^4$ | $R^5$ | $R^6$ | X'p | Xn | Y |
|---|---|---|---|---|---|---|---|
| B5-1 | H | H | H | H | — | — | O |
| B5-2 | Me | | H | H | — | — | O |
| B5-3 | Me | Me | H | H | — | — | O |
| B5-4 | Et | Me | H | H | — | — | O |
| B5-5 | n-Pr | Me | H | H | — | — | O |
| B5-6 | $CH_2$=CH | Me | H | H | — | — | O |
| B5-7 | Cl | Me | H | H | — | — | O |
| B5-8 | MeO | Me | H | H | — | — | O |
| B5-9 | H | H | Me | Me | — | — | O |
| B5-10 | Me | H | Me | Me | — | — | O |
| B5-11 | Me | Me | Me | Me | — | — | O |
| B5-12 | Me | Me | Cl | Cl | — | — | O |
| B5-13 | Cl | Cl | H | H | — | — | O |
| B5-14 | Cl | Cl | Cl | Cl | — | — | O |
| B5-15 | H | H | Cl | Cl | — | — | O |
| B5-16 | H | H | H | H | 5-F | — | O |
| B5-17 | H | H | H | H | 6-F | — | O |
| B5-18 | H | H | H | H | 7-Cl | — | O |
| B5-19 | H | H | H | H | 8-Cl | — | O |
| B5-20 | H | H | H | H | 5-Me | — | O |

TABLE 15

| Compound No. | $R^3$ | $R^4$ | $R^5$ | $R^6$ | X'p | Xn | Y |
|---|---|---|---|---|---|---|---|
| B5-21 | H | H | H | H | 6-Me | — | O |
| B5-22 | H | H | H | H | 6-MeO | — | O |
| B5-23 | H | H | H | H | 7-MeO | — | O |
| B5-24 | H | H | H | H | 5-OH | — | O |
| B5-25 | H | H | H | H | 6-OH | — | O |
| B5-26 | —$(CH_2)_5$— | | H | H | — | — | O |
| B5-27 | H | H | —$(CH_2)_5$— | | — | — | O |
| B5-28 | —$(CH_2)_4$— | | H | H | — | — | O |
| B5-29 | H | H | H | H | — | — | S |
| B5-30 | Me | Me | H | H | — | — | S |
| B5-31 | Me | Me | Me | Me | — | — | S |
| B5-32 | Cl | Cl | Cl | Cl | — | — | S |
| B5-33 | —$(CH_2)_5$— | | H | H | — | — | S |
| B5-34 | H | H | Me | Me | 8-F | — | O |

TABLE 16

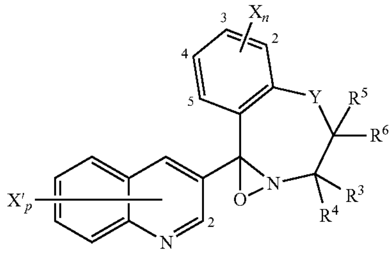

| Compound No. | $R^3$ | $R^4$ | $R^5$ | $R^6$ | X'p | Xn | Y |
|---|---|---|---|---|---|---|---|
| B6-1 | H | H | H | H | — | — | O |
| B6-2 | Me | H | H | H | — | — | O |
| B6-3 | Me | Me | H | H | — | — | O |
| B6-4 | Et | Me | H | H | — | — | O |
| B6-5 | n-Pr | Me | H | H | — | — | O |
| B6-6 | $CH_2$═CH | Me | H | H | — | — | O |
| B6-7 | Cl | Me | H | H | — | — | O |
| B6-8 | MeO | Me | H | H | — | — | O |
| B6-9 | H | H | Me | Me | — | — | O |
| B6-10 | Me | H | Me | Me | — | — | O |
| B6-11 | Me | Me | Me | Me | — | — | O |
| B6-12 | Me | Me | Cl | Cl | — | — | O |
| B6-13 | Cl | Cl | H | H | — | — | O |
| B6-14 | Cl | Cl | Cl | Cl | — | — | O |
| B6-15 | H | H | Cl | Cl | — | — | O |
| B6-16 | H | H | H | H | 5-F | — | O |
| B6-17 | H | H | H | H | 6-F | — | O |
| B6-18 | H | H | H | H | 7-Cl | — | O |
| B6-19 | H | H | H | H | 8-Cl | — | O |
| B6-20 | H | H | H | H | 5-Me | — | O |

TABLE 17

| Compound No. | $R^3$ | $R^4$ | $R^5$ | $R^6$ | X'p | Xn | Y |
|---|---|---|---|---|---|---|---|
| B6-21 | H | H | H | H | 6-Me | — | O |
| B6-22 | H | H | H | H | 6-MeO | — | O |
| B6-23 | H | H | H | H | 7-MeO | — | O |
| B6-24 | H | H | H | H | 5-OH | — | O |
| B6-25 | H | H | H | H | 6-OH | — | O |
| B6-26 | $—(CH_2)_5—$ | | H | H | — | — | O |
| B6-27 | H | H | $—(CH_2)_5—$ | | — | — | O |
| B6-28 | $—(CH_2)_4—$ | | H | H | — | — | O |
| B6-29 | H | H | H | H | — | — | S |
| B6-30 | Me | Me | H | H | — | — | S |
| B6-31 | Me | Me | Me | Me | — | — | S |
| B6-32 | Cl | Cl | Cl | Cl | — | — | S |
| B6-33 | $—(CH_2)_5—$ | | H | H | — | — | S |
| B6-34 | H | H | Me | Me | 8-F | — | O |

(Production Method of Compound of the Present Invention)

Although the compound of the present invention can be produced according to a known method, it can also be produced, for example, in the manner described below:

[CHEMICAL 13]

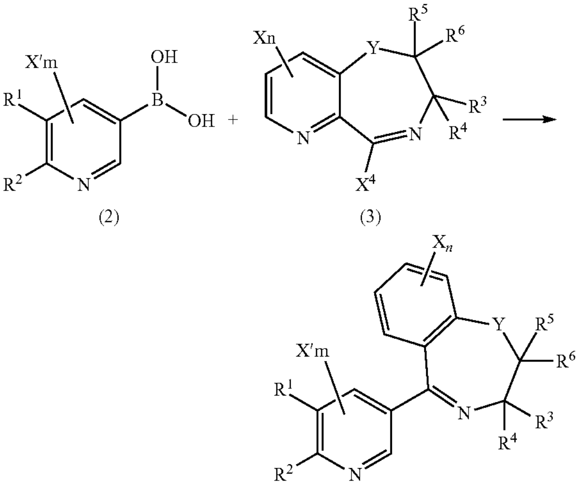

(2) (3)

(1)

(wherein, $R^1$ to $R^6$, X, X', Y, n and m are the same as previously defined, and $X^4$ represents a halogen atom).

A compound represented by formula (1) can be prepared by a Suzuki coupling reaction between a boronic acid derivative represented by formula (2) and an imidoyl halide derivative represented by formula (3) using a palladium complex described in the aforementioned Non-Patent Document 1 or Non-Patent Document 2.

Depending on the case, the imidoyl halide derivative represented by formula (3) may be coupled after deriving the halogen atom of $X^4$ to an alkylsulfonate group or haloalkylsulfonate group.

Here, a boronic acid derivative represented by the following formula (2') may be used instead of the boronic acid derivative represented by formula (2):

[CHEMICAL 14]

(2')

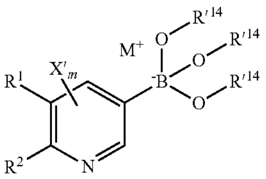

(wherein, $R^1$ to $R^2$, X' and in are the same as previously defined, $R'^{14}$ represents a C1-20 alkyl group, and M represents an alkaline metal such as lithium, sodium or potassium).

[CHEMICAL 15]

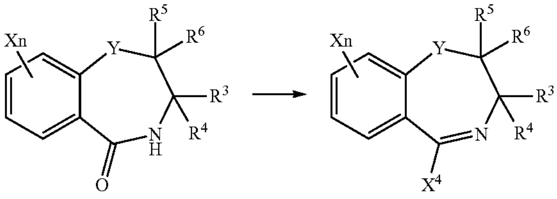

(4) (3)

(wherein, $R^3$ to $R^6$, X, Y and n are the same as previously defined, and $X^4$ represents a halogen atom.)

A compound represented by formula (3) can be prepared by a method in which a cyclic amide represented by formula (4) is reacted in the presence of an acid halide such as phosgene, oxalyl chloride or thionyl chloride. In addition, it may be similarly obtained using a mixed system of triphenylphosphine or carbon tetrachloride.

[CHEMICAL 16]

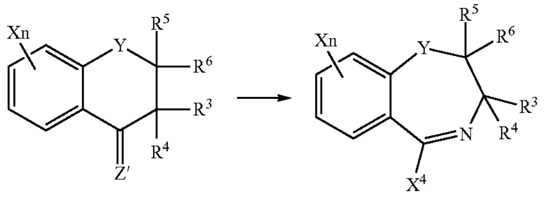

(5) (4)

(wherein, $R^3$ to $R^6$, X, Y and n are the same as previously defined, and Z' represents an oxygen atom or N—OH.)

A compound represented by formula (4) can be prepared by deriving a cyclic acetophenone derivative represented by formula (5) to an oxime by a Schmidt reaction, and then carrying out a Beckmann rearrangement. Various variations have been reported for both of these reactions. The Schmidt reaction can be carried out by, for example, reacting a ketone in sodium azide and a strong acid, such as concentrated hydrochloric acid, sulfuric acid, trifluoroacetic acid or methanesulfonic acid, and in the absence of a solvent or in a solvent such as acetonitrile, chloroform or methylene chloride, as described in Non-Patent Document 3 or Non-Patent Document 4.

In the Beckmann rearrangement, an oxime of a carbonyl compound is reacted with polyphosphoric acid or a trimethylsilyl ester thereof, or reacting at a high temperature with a Lewis acid such as aluminum triiodide or iron (III) chloride-impregnated montmorillonite in the absence of solvent or in the presence of a solvent such as acetonitrile. In addition, it can also be prepared by forming a mesylate or tosylate of an oxime followed by treating with a base such as aqueous sodium hydroxide solution or treating with a Lewis acid such as diethyl aluminum chloride.

The oxime can be prepared using a known method by reacting with hydroxylamine hydrochloride in a solvent such as ethanol followed by adding a base such as pyridine, sodium acetate or aqueous sodium hydroxide solution as necessary at a temperature up to the boiling point of the solvent.

In addition, a compound represented by formula (1') can be prepared by reacting a compound represented by formula (1) by (i) a contact hydrogenation method using a contact reduction catalyst such as palladium-carbon, platinum oxide or Raney nickel and hydrogen, or (ii) a reduction method using a metal-hydrogen compound such as lithium aluminum hydride or sodium borohydride.

[CHEMICAL 17]

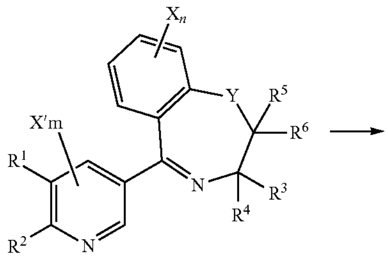

(1)

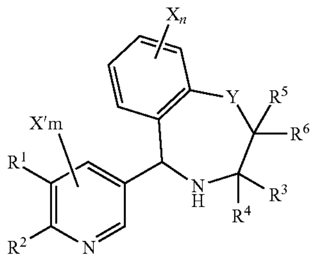

(1')

(wherein, $R^1$ to $R^6$, X, X', Y, n and m are the same as previously defined.)

(Intermediate Production Method)

The present invention also relates to a production method of a production intermediate used to produce a compound of the present invention. Namely, the present invention relates to a method in which a C1-6 alkyl magnesium halide and C1-6 alkyl lithium are reacted, followed by reacting a compound represented by formula (V):

[CHEMICAL 18]

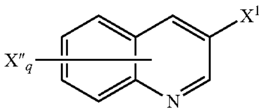

(V)

(wherein, X" each independently represents an unsubstituted or substituted C1-20 alkyl group, unsubstituted or substituted C2-20 alkenyl group, unsubstituted or substituted C2-20 alkynyl group, unsubstituted or substituted C3-20 cycloalkyl group, unsubstituted or substituted C4-20 cycloalkenyl group, unsubstituted or substituted C8-20 cycloalkynyl group, unsubstituted or substituted C6-10 aryl group, unsubstituted or substituted heterocyclic group, unsubstituted or substituted hydroxyl group, unsubstituted or substituted amino group, unsubstituted or substituted mercapto group, fluorine atom, chlorine atom or nitro group, q represents an integer of 0 to 6, and $X^1$ represents a bromine atom or iodine atom), followed by reacting a compound represented by formula (VI): $B(OR^{12})_3$ (wherein, $R^{12}$ each independently represents a C1-6 alkyl group) (to be referred to as a "trialkoxyborane reagent") to produce a boronic acid derivative represented by formula (VII):

[CHEMICAL 19]

(VII)

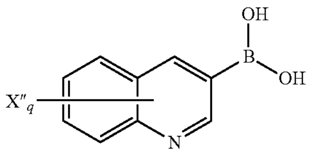

(wherein, X" and q are the same as previously defined).

This boronic acid derivative can be used as a production intermediate of the compound of the present invention.

Examples of the "C1-6 alkyl magnesium halide" used in the present invention include methyl magnesium chloride, ethyl magnesium chloride, n-propyl magnesium chloride, n-butyl magnesium chloride, s-butyl magnesium chloride, t-butyl magnesium chloride, n-butyl magnesium bromide and n-butyl magnesium iodide. A preferable example is n-butyl magnesium chloride. One type of these can be used alone or two or more types can be used in combination.

Examples of the "C1-6 alkyl lithium" used in the present invention include methyl lithium, ethyl lithium, n-propyl lithium, n-butyl lithium, s-butyl lithium and t-butyl A preferable example is n-butyl lithium. One type of these can be used alone or two or more types can be used in combination.

The amount of C1-6 alkyl magnesium halide used is 0.25 to 2 times and preferably 0.3 to 1.0 times the number of moles of the compound represented by formula (V). The amount of C1-6 alkyl lithium used is 2.0 to 2.5 times the number of moles of the C1-6 alkyl magnesium halide.

Examples of the unsubstituted or substituted C1-20 alkyl group, unsubstituted or substituted C2-20 alkenyl group, unsubstituted or substituted C2-20 alkynyl group, unsubstituted or substituted C3-20 cycloalkyl group, unsubstituted or substituted C4-20 cycloalkenyl group, unsubstituted or substituted C8-20 cycloalkynyl group, unsubstituted or substituted C6-10 aryl group, unsubstituted or substituted heterocyclic group, unsubstituted or substituted hydroxyl group, unsubstituted or substituted amino group and unsubstituted or substituted mercapto group of X" in formulas (V) and (VII) include the "groups" listed as examples of X of formula (I).

The "C1-6 alkyl group" of $R^{12}$ in formula (VI) refers to a linear or branched alkyl group having 1 to 6 carbon atoms. Examples include a methyl group, ethyl group, n-propyl group, n-butyl group, n-pentyl group, n-hexyl group, i-propyl group, i-butyl group, s-butyl group, t-butyl group, isopentyl group, neopentyl group, 2-methylbutyl group, 2,2-dimethylpropyl group and isohexyl group, and preferably a methyl group or i-propyl group.

The amount used of the trialkoxyborane reagent represented by formula (VI) is 1.0 to 2.5 times and preferably 1.0 to 1.2 times the number of moles of the compound represented by formula (V). One type of these can be used alone or two or more types can be used in combination.

In this reaction, the alkyl magnesium halide and two times the number of moles thereof of alkyl lithium form an ate complex in the reaction system, and this ate complex contributes to progression of the reaction. Consequently, in this reaction, a preferable method consists of initially forming an ate complex in the reaction system in advance followed by reacting a compound represented by formula CV), and then reacting the trialkoxyborane reagent.

There are no particular limitations on the solvent used in this reaction provided it does not inhibit the reaction, and hydrocarbon-based solvents such as hexane, cyclohexane, benzene or toluene, or ether-based solvents such as diethyl ether or THF, can be used. One type of these can be used alone or two or more types can be used in combination.

Although there are no particular limitations on the amount of solvent used, it is normally 1:3 to 1:100 and preferably 1:4 to 1:40 when represented as the ratio of [a compound represented by formula (V) (parts by weight)]:[the solvent (parts by volume)].

Although the reaction can be suitably carried out at a treatment temperature of −78° C. to room temperature, it is preferably carried out at −10 to 0° C.

In addition, a boronic acid ester derivative represented by formula (VII'):

[CHEMICAL 20]

(VII')

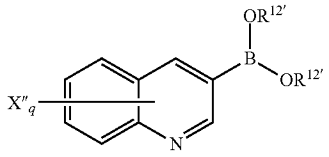

(wherein, X" and q are the same as previously defined, $R^{12'}$ each independently represents a C1-20 alkyl group, and $R^{12'}$ may mutually bond together to form a 5- to 8-membered ring) can also be used as a production intermediate of the compound of the present invention.

A boronic acid ester derivative represented by formula (VII') can be produced by esterifying a boronic acid derivative represented by the aforementioned formula (VII). A method described in Non-Patent Document 5 or Non-Patent Document 6, for example, can be used for the esterification method.

In either of these reactions, the target compound can be efficiently isolated by carrying out an ordinary post-treatment procedure in the field of organic synthesis chemistry and a conventionally known separation and purification means as necessary following completion of the reaction.

The structure of the target compound can be identified and confirmed by measurement of $^{1}$H-NMR spectrum, IR spectrum or mass spectrum and elementary analysis and the like.

(Production Intermediate)

The present invention also relates to a production intermediate of the compound of the present invention. Namely, the present invention relates to a boronic acid derivative represented by formula (VIII):

[CHEMICAL 21]

(VIII)

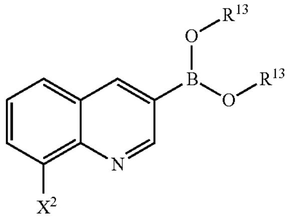

(wherein, $X^2$ represents a fluorine atom or chlorine atom, $R^{13}$ each independently represents a hydrogen atom or C1-20 alkyl group, and $R^{13}$ may mutually bond together to form a 5- to 8-membered ring).

This boronic acid derivative is particularly useful as a production intermediate of the compound of the present invention.

Examples of the "C1-20 alkyl group" of $R^{13}$ in formula (VIII) include the same "groups" listed as examples of C1-20 alkyl groups for X, and are preferably C1-6 alkyl groups such as a methyl group or i-propyl group.

Boronic acid derivatives represented by formula (VIII) can be produced according to the previously described production method.

Specific examples of boronic acid derivatives represented by formula (VIII) include the compounds listed in the following Table 18. Furthermore, in the table, Me represents a methyl group and i-Pr represents an i-propyl group.

TABLE 18

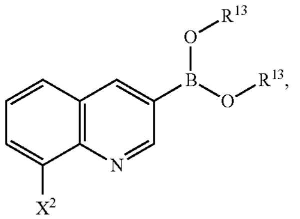

| Compound No. | $R^{13}$ | $R^{13'}$ | $X^2$ |
|---|---|---|---|
| C1-1 | H | H | F |
| C1-2 | H | H | Cl |
| C1-3 | Me | Me | F |
| C1-4 | Me | Me | Cl |
| C1-5 | i-Pr | i-Pr | F |
| C1-6 | $—(CH_2)_2—$ | | F |
| C1-7 | $—(CH_2)_3—$ | | F |
| C1-8 | $—(CH_2)_4—$ | | F |
| C1-9 | $—(CMe_2)_2—$ | | F |
| C1-10 | $—(CMe_2)_3—$ | | F |

The present invention also relates to a boronic acid derivative represented by formula (X):

[CHEMICAL 22]

(X)

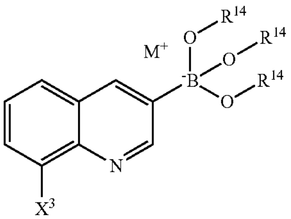

(wherein, $X^3$ represents a hydrogen atom, fluorine atom or chlorine atom, $R^{14}$ each independently represents a C1-20 alkyl group, $R^{14}$ may mutually bond together to form a 5- to 8-membered ring, and M represents an alkaline metal).

This boronic acid derivative is useful as a production intermediate of the compound of the present invention.

Examples of the "C1-20 alkyl group" of $R^{14}$ in formula (X) include the same "groups" listed as examples of C1-20 alkyl groups for X, and are preferably C1-6 alkyl groups such as a methyl group, ethyl group, n-propyl group or i-propyl group. Moreover, a boronic acid derivative represented by formula (X'):

[CHEMICAL 23]

(X')

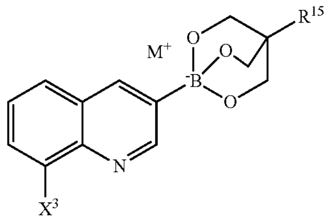

(wherein, $X^3$ represents a hydrogen atom, fluorine atom or chlorine atom, $R^{15}$ represents a C1-20 alkyl group, and M represents an alkaline metal), in which all three $R^{14}$ groups mutually bond together to form a ring, is more preferable.

Examples of the "C1-20 alkyl group" of $R^{15}$ in formula (X') include the same "groups" listed as examples of C1-20 alkyl groups for X, and are preferably C1-6 alkyl groups such as a methyl group, ethyl group, n-propyl group or i-propyl group.

Boronic acid derivatives represented by formula (X') can be produced using a method described in, for example, Non-Patent Document 7.

Specific examples of boronic acid derivatives represented by formula (X') include the compounds listed in the following Table 19.

TABLE 19

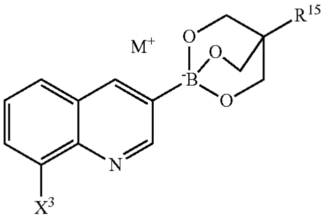

| Compound No. | $X^3$ | $R^{15}$ | M |
|---|---|---|---|
| C2-1 | F | H | K |
| C2-2 | F | Me | Li |
| C2-3 | F | Me | Na |
| C2-4 | F | Me | K |
| C2-5 | F | Et | K |
| C2-6 | Cl | H | K |
| C2-7 | Cl | Me | Li |
| C2-8 | Cl | Me | Na |
| C2-9 | Cl | Me | K |
| C2-10 | Cl | Et | K |
| C2-11 | H | Me | Na |
| C2-12 | H | Me | K |
| C2-13 | H | Et | K |

2) Fungicide for Agricultural and Horticultural Use

The present invention further relates to a fungicide for agricultural and horticultural use (which may also be referred to as "the fungicide of the present invention") that contains as an active ingredient thereof at least one type of nitrogen-containing heterocyclic compound of the present invention represented by formula (I), formula (IV) or formula (IX), or a salt thereof.

The fungicide of the present invention contains the compound of the present invention as an active ingredient thereof, and demonstrates superior fungicidal action against a wide range of types of fungi, such as fungi belonging to Oomycetes, Ascomycetes, Deuteromycetes or Basidiomycetes.

The fungicide of the present invention can be used to control various plant diseases occurring during cultivation of agricultural and horticultural crops including flowering plants, lawn grasses and pasture grasses by seed treatment, foliar spraying, soil application or water surface application and the like.

Examples of crops in which plant diseases can be controlled along with their plant diseases and causative organisms include:

Sugar Beets:
*Cercospora* leaf spot (*Cercospora beticola*)
*Aphanomyces* root rot (*Aphanomyces cochlloides*)
Root rot (*Thanatephorus cucumeris*)
Leaf blight (*Thanatephorus cucumeris*)
Peanuts:
Brown leaf spot (*Mycosphaerella arachidis*)
Black leaf blight (*Mycosphaerella berkeleyi*)
Cucumbers:
Powdery mildew (*Sphaerotheca fuliginea*)
Downy mildew (*Pseudoperonospora cubensis*)
Gummy stem blight (*Mycosphaerella melonis*)
*Fusarium* wilt (*Fusarium oxysporum*)
*Sclerotinia* rot (*Sclerotinia sclerotiorum*)
Gray mold (*Botrytis cinerea*)
Anthracnose (*Colletotrichum obriculare*)
Scab (*Cladosporium cucumerinum*)
*Corynespora* leaf spot (*Corynespora cassicola*)
Damping-off (*Pythiumdebaryanam, Rhizoctonia solani* Kuhn)
Bacterial spot (*Pseudomonas syringae* pv. *Lecrymans*)
Tomatoes:
Gray mold (*Botrytis cinerea*)
Leaf mold (*Cladosporium fulvum*)
Late blight (*Phytophthora infestans*)
Eggplants:
Gray mold (*Botrytis cinerea*)
Black rot (*Corynespora malongenae*)
Powdery mildew (*Erysiphe cichoracearum*)
Leaf mold (*Mycovellosiella nattrassii*)
Strawberries:
Gray mold (*Botrytis cinerea*)
Powdery mildew (*Sphaerotheca humuli*)
Anthracnose (*Colletotrichum acutatum, Colletotrichum fragariae*)
*Phytophthora* rot (*Phytophthora cactorum*)
Onions:
Neck rot (*Botrytis allii*)
Gray mold (*Botrytis cinerea*)
Leaf blight (*Botrytis squamosa*)
Downy mildew (*Peronospora destructor*)
Cabbage:
Clubroot (*Plasmodiophora brassicae*)
Bacterial soft rot (*Erwinia carotovora*)
Downy mildew (*Peronospora parasitica*)
Kidney Beans:
Stem rot (*Sclerotinia sclerotiorum*)
Gray mold (*Botrytis cinerea*)
Apples:
Powdery mildew (*Podosphaera leucotricha*)
Scab (*Venturia inaequalis*)
Blossom blight (*Monilinia mali*)
Fruit spot (*Mycosphaerella pomi*)
*Valsa* canker (*Valsa mali*)
*Alternaria* blotch (*Alternaria mali*)
Rust (*Gymnosporangium yamadae*)
Ring rot (*Botryosphaeria berengeriana*)
Anthracnose (*Glomerella cingulata, Colletotrichum acutatum*)
Blotch (*Diplocarpon mali*)
Fly speck (*Zygophiala jamaicensis*)
Sooty blotch (*Gloeodes pomigena*)
Persimmons:
Powdery mildew (*Phyllactinia kakicola*)
Anthracnose (*Gloeosporium kaki*)
Angular leaf spot (*Cercospora kaki*)
Peaches:
Brown rot (*Monilinia fructicola*)
Scab (*Cladosporium carpophilum*)
*Phomopsis* rot (*Phomopsis* sp.)
Cherries:
Brown rot (*Monolinia fructicola*)
Grapes:
Gray mold (*Botrytis cinerea*)
Powdery mildew (*Uncinula necator*)
Ripe rot (*Glomerella cingulata, Colletotrichum acutatum*)
Downy mildew (*Plasmopara viticola*)
Anthracnose (*Elsinoe ampelina*)
Leaf blight (*Pseudocercospora vitis*)
Black rot (*Guignardia bidwellii*)
Pears:
Scab (*Venturia nashicola*)
Rust (*Gymnosporangium asiaticum*)
Black spot (*Alternaria kikuchiana*)
Ring rot (*Botryosphaeria berengeriana*)
Powdery mildew (*Phyllactinia mali*)
Tea:
Gray blight (*Pestalotia theae*)
Anthracnose (*Collectotrichum theae-sinensis*)
Citrus:
Scab (*Elsinoe fawcette*)
Blue mold (*Penicillium italicum*)
Common green mold (*Penicillium digitatum*)
Gray mold (*Botrytis cinerea*)
Melanose (*Diaporthe citri*)
Canker (*Xanthomonas campestris* pv. *Citri*)
Wheat:
Powdery mildew (*Erysiphe graminis* f. sp. *tritici*)
*Fusarium* blight (*Gibberella zeae*)
Leaf rust (*Puccinia recondita*)
Browning root rot (*Pythium iwayamai*)
Snow mold (*Monographella nivalis*)
Eye spot (*Pseudocercosporella herpotrichoides*)
Speckled leaf blotch (*Septoria tritici*)
Glume blotch (*Leptosphaeria nodorum*)
*Typhula* snow blight (*Typhula incarnata*)
*Sclerotinia* snow blight (*Myriosclerotinia borealis*)
Take-all (*Gaeumanomyces graminis*)
Barley:
Stripe (*Pyrenophora graminea*)
Leaf blotch (*Rhynchosporium secalis*)
Loose smut (*Ustilago tritici, U. nuda*)
Rice:
Blast (*Pyricularia oryzae*)
Sheath blight (*Rhizoctonia solani*)
Bakanae disease (*Gibberella fujikuroi*)
Brown spot (*Cochliobolus niyabeanus*)
Seedling blight (*Pythium graminicolum*)
Bacterial leaf blight (*Xanthomonas oryzae*)
Bacterial seedling blight (*Burkholderia plantarii*)
Bacterial brown stripe (*Acidovorax avanae*)
Bacterial grain rot (*Burkholderia glumae*)
Tobacco:
*Sclerotinia* stem-rot (*Sclerotinia sclerotiorum*)

Powdery mildew (*Erysiphe cichoracearum*)
Tulips:
Gray mold (*Botrytis cinerea*)
Bent Grass:
*Sclerotinia* snow blight (*Sclerotinia borealis*)
Bacterial shoot blight (*Pythium aphanidermatum*)
Orchard Grass:
Powdery mildew (*Erysiphe graminis*)
Soybeans:
Purple stain (*Cercospora kikuchii*)
Downy mildew (*Peronospora Manshurica*)
*Phytophthora* root and stem rot (*Phytophthora sojae*)
Potatoes, Tomatoes:
Late blight (*Phytophthora infestans*)

In addition, various pathogens have recently developed resistance to benzimidazole fungicides, dicarboximide fungicides and the like resulting in inadequate efficacy of these drugs, thereby creating the need for effective drugs against resistant organisms as well. The fungicide of the present invention also has superior fungicidal effects against resistant organisms in addition to pathogens that are sensitive to these drugs.

For example, the fungicide of the present invention is effective against gray mold (*Botrytis cinerea*), sugar beet *cercospora* leaf spot (*Cercospora beticola*) and apple scab (*Venturia inaequalis*), pear scab (*Venturia nashicola*), which exhibit resistance to benzimidazole fungicides such as thiophanate-methyl, benomyl and carbendazim, in the same manner as sensitive organisms.

Moreover, the fungicide of the present invention is effective against gray mold (*Botrytis cinerea*), which exhibits resistance to dicarboximide fungicides (such as vinclozoline, procymidone and iprodione) in the same manner as sensitive organisms.

Examples of diseases for which application of the fungicide of the present invention is more preferable include apple scab, cucumber gray mold, wheat powdery mildew, tomato late blight, wheat leaf rust, rice blast and cucumber *fusarium* wilt.

In addition, the fungicide of the present invention causes little chemical damage, exhibits low toxicity to fish and warm-blooded animals, and has a high degree of safety.

During actual application, the fungicide of the present invention may be used in the pure form of a compound of the present invention without adding other components, or may be used in a form able to be adopted by an ordinary agricultural chemical for the purpose of using as an agricultural chemical, namely an agricultural chemical preparation such as a wettable powder, granules, powder, emulsion, aqueous solution, suspension or water-dispersible granules.

Examples of additives and carriers able to be added to the agricultural chemical preparation in the case using for the purpose of solid formulations include vegetable powders such as soybean powder or wheat powder, mineral fine powders such as diatomaceous earth, apatite, gypsum, talc, bentonite, pyrophyllite or clay, and organic and inorganic compounds such as sodium benzoate, urea or sodium sulfate.

In addition, in the case of using for the purpose of liquid formulations, kerosene, xylene and petroleum-based aromatic hydrocarbons, cyclohexane, cyclohexanone, dimethylformamide, dimethylsulfoxide, alcohol, acetone, trichloroethylene, methyl isobutyl ketone, mineral oil, vegetable oil and water, for example, can be used as solvents.

Moreover, a surfactant can be added to these preparations as necessary to obtain a uniform and stable form.

There are no particular limitations on surfactants able to be added, and examples include nonionic surfactants such as polyoxyethylene-alkyl phenyl ethers, polyoxyethylene-alkyl ethers, polyoxyethylene-higher fatty acid esters, polyoxyethylene-sorbitan fatty acid esters or polyoxyethylene-tristyryl phenyl ether, and sulfuric acid ester salts of polyoxyethylene-alkyl phenyl ethers, alkyl benzene sulfonates, sulfuric acid ester salts of higher alcohols, alkyl naphthalene sulfonates, polycarboxylates, lignin sulfonates, formaldehyde condensates of alkyl naphthalene sulfonates and isobutylene-maleic anhydrate copolymers.

Wettable powders, emulsions, flowable agents, aqueous solutions and water-dispersible granules obtained in this manner are used in the form of solutions, suspensions or emulsions by diluting to a prescribed concentration with water, while powders and granules are used by spraying directly onto plants.

Normally, the amount of active ingredient in the fungicide of the present invention is preferably 0.01 to 90% by weight and more preferably 0.05 to 85% by weight based on the total weight of the composition (preparation).

Although the applied amount of the fungicide of the present invention varies according to weather conditions, preparation form, application time, application method, applied location, target control disease, target crop and the like, it is normally 1 to 1,000 g and preferably 10 to 100 g as the amount of active ingredient compound per hectare.

In the case of applying by diluting a wettable powder, emulsion, suspension, aqueous solution or water-dispersible granules with water, the applied concentration is 1 to 1000 ppm and preferably 10 to 250 ppm.

In addition to the compound of the present invention, the fungicide of the present invention can also be mixed with one type or two or more types of various fungicides, insecticides, miticides or synergists.

Typical examples of fungicides, insecticides, miticides and plant growth regulators able to be used by mixing with the compound of the present invention are indicated below.

Fungicides:

benzimidazole-based fungicides such as benomyl, carbendazim, fuberidazole, thiabendazole or thiophanate-methyl;

dicarboxylmide-based fungicides such as chlozolinate, iprodione, procymidone or vinclozolin;

DMI-fungicides such as imazalil, oxpoconazole, pefurazoate, prochloraz, triflumizole, triforine, pyrifenox, fenarimol, nuarimol, azaconazole, bitertanol, bromuconazole, cyproconazole, difenoconazole, diniconazole, epoxiconazole, fenbuconazole, fluquinconazole, flusilazole, flutriafol, hexaconazole, imibenconazole, ipconazole, metconazole, myclobutanil, penconazole, propiconazole, prothioconazole, simeconazole, tebuconazole, tetraconazole, triadimefon, triadimenol, triticonazole, etaconazole, furconazole-cis, ipconazole or imibenconazole;

phenylamide-based fungicides such as benalaxyl, furalaxyl, metalaxyl, metalaxyl-M, oxadixyl or ofurace;

amine-based fungicides such as aldimorph, dodemorph, fenpropimorph, tridemorph, fenpropidin, piperalin or spiroxamine;

phosphothioate-based fungicides such as EDDP, iprobenfos or pyrazophos;

dithiolane-based fungicides such as isoprothiolane;

carboxamide-based fungicides such as benodanil, boscalid, carboxin, fenfuram, flutolanil, furametpyr, mepronil, oxycarboxin, penthiopyrad or thifluzamide;

hydroxy-(2-amino)pyrimidine-based fungicides such as bupirimate, dimethirimol or ethirimol;

AP (anilinopyrimidine)-based fungicides such as cyprodinil, mepanipyrim or pyrimethanil;

N-phenylcarbamate-based fungicides such as diethofencarb;

QoI-based fungicides (Qo inhibitors) such as azoxystrobin, picoxystrobin, pyraclostrobin, kresoxim-methyl, trifloxystrobin, dimoxystrobin, metominostrobin, orysastrobin, famoxadone, fluoxastrobin, fenamidone, metominofen or pyribencarb;

PP (phenylpyrrole)-based fungicides such as fenpiclonil or fludioxonil;

quinoline-based fungicides such as quinoxyfen;

AH (aromatic hydrocarbon)-based fungicides such as biphenyl, chloroneb, dicloran, quintozene, tecnazene or tolclofos-methyl;

MBI-R-based fungicides such as fthalide, pyroquilon or tricyclazole;

MBI-D-based fungicides such as carpropamid, diclocymet or fenoxanil;

SBI-based fungicides such as fenhexamid, pyributicarb or terbinafine;

phenylurea-based fungicides such as pencycuron;

QiI-based fungicides (Qi inhibitors) such as cyazofamid;

benzamide-based fungicides such as zoxamide;

enopyranuron-based fungicides such as blasticidin or mildiomycin;

hexopyranosyl-based fungicides such as kasugamycin;

glucopyranosyl-based fungicides such as streptomycin or validamycin;

cyanoacetoamide-based fungicides such as cymoxanil;

carbamate-based fungicides such as propamocarb, prothiocarb or polycarbamate;

uncoupling agent-based fungicides such as binapacryl, dinocap, ferimzone or fluazinam;

organic tin compound-based fungicides such as triphenyltin acetate, triphenyltin chloride or triphenyltin hydroxide;

phosphoric acid esters such as phosphorous acid, tolclofos-methyl or fosetyl;

phthalamic acid-based fungicides such as tecloftalam;

benzotriazine-based fungicides such as triazoxide;

benzenesulfonamide-based fungicides such as flusulfamide;

pyridazinone-based fungicides such as diclomezine;

CAA (carbonic acid amide)-based fungicides such as dimethomorph, flumorph, benthiavalicarb, iprovalicarb or mandipropamid;

tetracycline-based fungicides such as oxytetracycline;

thiocarbamate-based fungicides such as metasulfocarb; and fungicides based on other compounds such as etridiazole, polyoxin, oxolinic acid, hydroxyisoxazole, octhilinone, silthiofam, diflumetorim, acibenzolar-S-methyl, probenazole, tiadinil, ethaboxam, cyflufenamid, proquinazid, metrafenone, fluopicolide, copper hydroxide, organic copper, sulfur, ferbam, manzeb, maneb, metiram, propineb, thiuram, zineb, ziram, captan, captafol, folpet, chlorothalonil, dichlofluanid, tolylfluanid, dodine, guazatine, iminoctadine, anilazine, dithianon, chloropicrin, dazomet, metam sodium salt, qinomethionate, cyprofuram, silthiofam, *agrobacterium* or fluoroimide.

Insecticides/Miticides:

Organic phosphorous and carbamate-based insecticides: fenthion, fenitrothion, diazinon, chlorpyrifos, ESP, vamidothion, phenthoate, dimethoate, formothion, malathion, trichlorfon, thiometon, phosmet, dichlorvos, acephate, EPBP, methyl parathion, oxydemetone methyl, ethion, salithion, cyanophos, isoxathion, pyridafenthion, phosalone, methidathion, sulprofos, chlorfenvinphos, tetrachlorovinphos, dimethylvinphos, propaphos, isofenphos, ethyl thiometon, profenofos, pyraclofos, monocrotophos, azinphos-methyl, aldicarb, methomyl, thiodicarb, carbofuran, carbosulphan, benfuracarb, furathiocarb, propoxur, BPMC, MTMC, MIPC, carbaryl, pirimicarb, ethiophencarb, phenoxycarb, EDDP, and the like.

Pyrethroid-based insecticides: permethrin, cypermethrin, deltamethrin, fenvalerate, fenpropathrin, pyrethrin, allethrin, tetramethrin, resmethrin, dimethrin, propathrin, phenothrin, prothrin, fluvalinate, cyfluthrin, cyhalothrin, flucythrinate, etofenprox, cycloprothrin, tralomethrin, silafluofen, flufenprox, acrinathrin, and the like.

Benzoylurea-based and other insecticides: diflubenzuron, chlorfluazuron, hexaflumuron, triflumuron, tetrabenzuron, flufenoxuron, flucycloxuron, buprofezin, pyriproxyfen, methoprene, benzoepin, diafenthiuron, acetamiprid, imidacloprid, nitenpyram, fipronil, cartap, thiocyclam, bensultap, nicotine sulfate, rotenone, metaldehyde, machine oil, BT and microbial agrichemicals such as insect pathogenic viruses.

Nematocides:

Fenamiphos, fosthiazate, and the like

Miticides:

Chlorobenzilate, phenisobromolate, dicofol, amitraz, BPPS, benzomate, hexythiazox, fenbutatin oxide, polynactin, chinomethionate, CPCBS, tetradifon, avermectin, milbemectin, clofentezine, cyhexatin, pyridaben, fenpyroximate, tebufenpyrad, pyrimidifen, fenothiocarb, dienochlor, and the like.

Plant Growth Regulators:

abscisic acid, indolebutyric acid, uniconazole, ethychlozate, ethephon, cloxyfonac, chlormequat, *chlorella* extract, calcium peroxide, cyanamide, dichlorprop, gibberellin, daminozide, decyl alcohol, trinexapac-ethyl, mepiquat chloride, paclobutrazol, paraffin, wax, piperonylbutoxide, pyraflufen-ethyl, flurprimidol, prohydrojasmon, prohexadione calcium salt, benzylaminopurine, pendimethalin, forchlorfenuron, maleic hydrazide potassium, 1-naphthylacetoamide, 4-CPA, MCPB, choline, oxyquinoline sulfate, ethychlozate, butoralin, 1-methylcyclopropene, aviglycine hydrochloride.

EXAMPLES

Although the following provides a more detailed explanation of the present invention by indicating examples thereof, the present invention is not limited to the following examples. Furthermore, compound numbers of the examples correspond to the compound numbers in the aforementioned tables listing examples of compounds.

(Compound Synthesis)

Example 1

2,2-Dimethyl-5-(3-quinolinyl)-2,3-dihydro-benzo[f][1,4]oxazepine (Compound No. B1-9)

(Step 1)

After adding phosphorous oxychloride (5 mL) and phosphorous pentachloride (0.65 g, 3.13 mmol) to 2,2-dimethyl-3,4-dihydro-2H-benzo[f][1,4]oxazepin-5-one (0.60 g, 3.13 mmol) (refer to the aforementioned Non-Patent Document 3 for a description of the synthesis method) at room temperature, the mixture was refluxed while heating for 5.5 hours. After allowing to cool to room temperature, the mixture was concentrated under reduced pressure and the residue was poured over crushed ice. The aqueous layer was extracted with ethyl acetate (50 mL) and the combined organic layer was washed twice with "saturated aqueous sodium bicarbonate solution (30 mL)+$H_2O$ (20 mL) and then with brine (30 mL) followed by drying with magnesium sulfate. After filtering, the solvent was distilled off under reduced pressure to obtain 0.74 g of 5-chloro-2,2-dimethyl-2,3-dihydro-benzo[f][1,4]oxazepine in the form of a brown oily substance. This substance was used in the next reaction without purifying further.

(Step 2)

After carrying out nitrogen replacement on a dimethylformamide solution (15 mL) of 3-quinoline boronic acid (0.70 g, 4.07 mmol) and 2 M aqueous cesium carbonate solution (4.70 mL, 9.40 mol), tetrakis(triphenylphosphine)palladium (0.72 g, 0.63 mmol) and 5-chloro-2,2-dimethyl-2,3-dihydro-benzo[f][1,4]oxazepine (3.13 mmol) were added to this solution. This solution was then stirred for 14 hours while heating at 90° C. Subsequently, the reaction solution was cooled to room temperature followed by pouring in ethyl acetate (50 mL) and water (50 ml) and filtering with celite. The filtrate was extracted with ethyl acetate (100 mL) and the organic layer was washed with brine (50 mL) followed by drying with magnesium sulfate. After filtering, the solvent was distilled off under reduced pressure to obtain 0.50 g (53%) of the target compound by purifying the resulting residue by silica gel column chromatography (hexane:ethyl acetate=2:1).

Physical properties: mp 134-135° C.

The following compound was synthesized using the same method as Example 1.

Example 2

3,3-Dimethyl-5-(3-quinolinyl)-2,3-dihydro-benzo[f][1,4]oxazepine (Compound No. B1-3)

Physical properties: mp 109-112° C.

Example 3

2-Chloro-2,3-dimethyl-5-(3-quinolinyl)-2,3-dihydro-benzo[f][1,4]oxazepine (Compound No. B1-29)

7.7 g (40.3 mmol) of 2-ethyl-2-methyl-2,3-dihydro-4H-1,3-benzoxazin-4-one were dissolved in 30 mL of phosphorous oxychloride followed by the addition of 8.4 g (40.3 mmol) of phosphorous pentachloride and refluxing while heating for 4 hours. After concentrating the reaction solution under reduced pressure, the residue was dissolved in ethyl acetate and sequentially washed with aqueous sodium bicarbonate solution and saturated saline. After drying the organic layer with magnesium sulfate, the solvent was distilled off under reduced pressure. 3.4 g (22.4 mmol) of 3-quinoline boronic acid, 21.9 g (67.2 mmol) of cesium carbonate and 5.2 g (4.48 mmol) of tetrakis(triphenylphosphine)palladium were dissolved in a mixed solution of 120 mL of DMF and 30 mL of water, and 4.7 g of the resulting residue were added to this mixed solution. After carrying out nitrogen replacement on the reaction solution, the reaction solution was stirred for 14 hours at 80 to 90° C. After cooling the reaction solution to room temperature, the reaction solution was poured into ice water and extracted with ethyl acetate. After washing the organic layer with saturated saline, the solvent was distilled off under reduced pressure and the resulting residue was purified by silica gel column chromatography (developing solvent; chloroform:ethyl acetate=4:1) to obtain mutual stereoisomers consisting of 0.15 g of Compound (A) (yield: 2%) and 0.15 g of Compound (B) (yield: 2%).

Physical properties of Compound (A): amorphous $^1$H-NMR (300 MHz, $CDCl_3$) δ: 1.67 (d, 2H, J=6.8 Hz), 1.72 (s, 3H), 4.41 (q, 2H, J=6.8 Hz), 6.9-7.1 (m, 2H), 7.25 (dd, 1H, J=7.4, 2.4 Hz), 7.44 (m, 1H), 7.62 (m, 1H), 7.80 (m, 1H), 7.87 (m, 1H), 8.18 (d, 1H, J=8.3 Hz), 8.39 (d, 1H, J=2.0 Hz), 9.14 (d, 1H, J=2.0 Hz)

MS (APCI, m/z): 337 ([M+1]$^+$)

Physical properties of Compound (B): amorphous $^1$H-NMR (300 MHz, $CDCl_3$) δ: 1.73 (d, 2H, J=6.5 Hz), 1.72 (s, 3H), 4.38 (q, 2H, J=6.5 Hz), 6.90-7.05 (m, 2H), 7.25 (dd, 1H, J=8.0, 1.5 Hz), 7.45 (m, 1H), 7.62 (m, 1H), 7.80 (m, 1H), 7.90 (d, 1H, J=8.0 Hz), 8.18 (d, 1H, J=8.6 Hz), 8.38 (d, 1H, J=1.8 Hz), 9.14 (d, 1H, J=2.4 Hz)

MS (APCI, m/z): 337 ([M+1]$^+$)

The following compounds were produced using the same method as Example 3.

Example 4

2-Chloro-9-fluoro-2-methyl-5-(3-quinolinyl)-2,3-dihydro-benzo[f][1,4]oxazepine (Compound No. B1-30)

Physical properties: mp 123-125° C.

Example 5

5-(3-Quinolinyl)-2,3,3,3-tetramethyl-2,3-dihydro-benzo[f][1,4]oxazepine (Compound No. B1-11)

Physical properties: mp 135-137° C.

Example 6

5-(3-Quinolinyl)-2,3-dihydro-benzo[f][1,4]oxazepine (Compound No. B1-1)

Physical properties: mp 115-117° C.

Example 7

2-Ethyl-2-methyl-5-(3-quinolinyl)-2,3-dihydro-benzo[f][1,4]oxazepine (Compound No. B1-31)

Physical properties: amorphous $^1$H-NMR (300 MHz, $CDCl_3$) δ: 1.08 (t, 3H, J=7.5 Hz), 1.43 (s, 3H), 1.74-1.90 (m, 2H), 3.60 (d, 1H, J=11.7 Hz), 3.64 (d, 1H, J=11.7 Hz), 7.11-7.21 (m, 3H), 7.47 (m, 1H), 7.56 (m, 1H), 7.76 (m, 1H), 7.82 (d, 1H, J=8.1 Hz), 8.15 (d, 1H, J=8.4 Hz), 8.31 (d, 1H, J=2.4 Hz), 9.28 (d, 1H, J=2.4 Hz)

MS (APCI, m/z): 317 ([M+1]$^+$)

Example 8

2,2-Diethyl-5-(3-quinolinyl)-2,3-dihydro-benzo[f][1,4]oxazepine (Compound No. B1-32)

Physical properties: amorphous $^1$H-NMR (300 MHz, $CDCl_3$) δ: 1.04 (t, 3H, J=7.5 Hz), 1.76-1.84 (m, 2H), 3.63 (s, 2H), 7.10-7.19 (m, 3H), 7.46 (m, 1H), 7.55 (m, 1H), 7.72-7.82 (m, 2H), 8.15 (d, 1H, J=8.4 Hz), 8.29 (d, 1H, J=2.1 Hz), 9.27 (d, 1H, J=2.1 Hz)

MS (APCI, m/z): 331 ([M+1]$^+$)

Example 9

2-Isopropyl-2-methyl-5-(3-quinolinyl)-2,3-dihydro-benzo[f][1,4]oxazepine (Compound No. B1-35)

Physical properties: amorphous $^1$H-NMR (300 MHz, $CDCl_3$) δ: 1.02 (d, 3H, J=6.8 Hz), 1.13 (d, 3H, J=6.8 Hz), 1.35 (s, 3H), 2.18 (m, 1H), 3.63 (d, 1H, J=11.6 Hz), 3.74 (d, 1H, J=11.6 Hz), 7.12-7.20 (m, 3H), 7.47 (m, 1H), 7.56 (m, 1H), 7.60 (m, 1H), 7.82 (d, 1H, J=8.0 Hz) 8.16 (d, 1H, J=8.6 Hz), 8.31 (d, 1H, J=2.4 Hz), 9.27 (d, 1H, J=2.4 Hz)

MS (APCI, m/z): 331 ($[M+1]^+$)

Example 10

5-(8-Fluoro-quinolin-3-yl)-2,2-dimethyl-2,3-dihydro-benzo[f][1,4]oxazepine (Compound No. B1-37)

Physical properties: mp 165-167° C.

Example 11

2,2-Dimethyl-9-fluoro-5-(8-fluoro-quinolin-3-yl)-2,3-dihydro-benzo[f][1,4]oxazepine (Compound No. B1-38)

Physical properties: mp 171-173° C.

Example 12

2,2-Dimethyl-9-chloro-5-(8-chloro-quinolin-3-yl)-2,3-dihydro-benzo[f][1,4]oxazepine (Compound No. B1-41)

Physical properties: mp 214-217° C.

Example 13

5-(3-Quinolinyl)-2,2,3-trimethyl-2,3-dihydro-benzo[f][1,4]oxazepine (Compound No. B1-42)

Physical properties: mp 139-142° C.

Example 14

9-Fluoro-5-(3-quinolinyl)-2,2,3,3-tetramethyl-2,3-dihydro-benzo[f][1,4]oxazepine (Compound No. B1-43)

Physical properties: mp 132-133° C.

Example 15

9-Fluoro-5-(8-fluoro-quinolin-3-yl)-2,2,3,3-tetramethyl-2,3-dihydro-benzo[f][1,4]oxazepine (Compound No B1-45)

Physical properties: mp 144-145° C.

Example 16

5-(8-Chloro-quinolin-3-yl)-2,2-dimethyl-2,3-dihydro-benzo[f][1,4]oxazepine (Compound No. B1-46)

Physical properties: mp 155-157° C.

Example 17

2-Ethyl-5-(8-fluoro-quinolin-3-yl)-2-methyl-2,3-dihydro-benzo[f][1,4]oxazepine (Compound No. B1-47)

Physical properties: mp 93-95° C.

Example 18

5-(8-Fluoro-quinolin-3-yl)-2,2,3,3-tetramethyl-2,3-dihydro-benzo[f][1,4]oxazepine (Compound No. B1-50)

Physical properties: mp 138-140° C.

Example 19

2,2-Dimethyl-5-(3-quinolinyl)-2,3-dihydro-benzo[f][1,4]thiazepine (Compound No. B2-6)

The 2,2-dimethyl-3,4-dihydro-2H-benzo[f][1,4]thiazepin-5-one used in the reaction was prepared with reference to the method described in the aforementioned Non-Patent Document 8.

Physical properties: mp 125-128° C.

Example 20

2,2-Dimethyl-5-(8-fluoro-quinolin-3-yl)-2,3-dihydro-benzo[f][1,4]thiazepine (Compound No. B2-13)

Physical properties: mp 181-183° C.

Example 21

2,2-Dimethyl-9-fluoro-5-(quinolin-3-yl)-2,3-dihydro-benzo[f][1,4]oxazepine (Compound No. B1-36)

Physical properties: amorphous $^1$H-NMR (300 MHz, $CDCl_3$) δ: 1.54 (s, 6H), 3.65 (s, 2H), 6.9-7.9 (m, 6H), 8.16 (d, 1H, J=8.6 Hz), 8.34 (d, 1H, J=2.1 Hz), 9.32 (d, 1H, J=2.1 Hz)

Example 22

9-Chloro-2,2-dimethyl-5-(quinolin-3-yl)-2,3-dihydro-benzo[f][1,4]oxazepine (Compound No. B1-34)

Physical properties: amorphous $^1$H-NMR (300 MHz, $CDCl_3$) δ: 1.56 (s, 6H), 3.66 (s, 2H), 7.0-7.2 (m, 2H), 7.5-7.9 (m, 4H), 8.16 (d, 1H, J=8.6 Hz), 8.28 (d, 1H, J=2.1 Hz), 9.26 (d, 1H, J=2.1 Hz)

Example 23

2,2-Dimethyl-9-methyl-5-(quinolin-3-yl)-2,3-dihydro-benzo[f][1,4]oxazepine (Compound No. B1-33)

Physical properties: amorphous $^1$H-NMR (300 MHz, $CDCl_3$) δ: 1.51 (s, 6H), 2.37 (s, 3H), 3.64 (s, 2H), 6.9-7.1 (m, 2H), 7.3-7.9 (m, 4H), 8.15 (d, 1H, J=8.0 Hz), 8.29 (d, 1H, J=2.1 Hz), 9.26 (d, 1H, J=2.1 Hz)

Example 24

2,2-Dimethyl-5-(quinolin-3-yl)-9-trifluoromethyl-2,3-dihydro-benzo[f][1,4]oxazepine (Compound No. B1-44)

Physical properties: amorphous $^1$H-NMR (300 MHz, $CDCl_3$) δ: 1.54 (s, 6H), 3.78 (s, 2H), 7.1-7.9 (m, 6H), 8.16 (d, 1H, J=8.0 Hz), 8.22 (d, 1H, J=2.4 Hz), 9.22 (d, 1H, J=2.4 Hz)

Example 25

9-Chloro-2,2-dimethyl-5-(8-methylquinolin-3-yl)-2,3-dihydro-benzo[f][1,4]oxazepine (Compound No. B1-40)

Physical properties: mp 145-147° C.

$^1$H-NMR (300 MHz, $CDCl_3$) δ: 1.56 (s, 6H), 2.84 (s, 3H), 3.65 (s, 2H), 7.0-7.2 (m, 2H), 7.4-7.7 (m, 4H), 8.30 (d, 1H, J=2.3 Hz), 9.21 (d, 1H, J=2.3 Hz)

Example 26

2-Ethyl-9-fluoro-5-(8-fluoro-quinolin-3-yl)-2-methyl-2,3-dihydro-benzo[f][1,4]oxazepine (Compound No. B1-49)

Physical properties: mp 140-142° C.

Example 27

9-Chloro-5-(8-fluoro-quinolin-3-yl)-2,2-dimethyl-2,3-dihydro-benzo[f][1,4]oxazepine (Compound No. B1-39)

Physical properties: mp 190-191° C.

Example 28

9-Chloro-2-ethyl-5-(8-fluoro-quinolin-3-yl)-2-methyl-2,3-dihydro-benzo[f][1,4]oxazepine (Compound No. B1-48)

Physical properties: mp 144-146° C.

Example 29

9-Chloro-2,2-dimethyl-5-(5',6',7',8'-tetrahydroquinolin-3-yl)-2,3-dihydro-benzo[f][1,4]oxazepine (Compound No. A1-19)

Physical properties: amorphous $^1$H-NMR (300 MHz, $CDCl_3$) δ: 1.53 (s, 6H), 1.7-2.0 (m, 4H), 2.79 (t, 2H), 2.96 (t, 2H), 3.56 (s, 2H), 7.0-7.1 (m, 2H), 7.54 (dd, 1H, J=2.1, 7.7 Hz), 7.65 (d, 1H, J=2.1 Hz), 8.47 (d, 1H, J=2.1 Hz)

Example 30

9-Chloro-2,2-dimethyl-5-(thieno[2,3-b]pyridin-5-yl)-2,3-dihydro-benzo[f][1,4]oxazepine (Compound No. A1-20)

The 5-bromothieno[2,3b]pyridine used in the reaction was prepared with reference to the method described in the aforementioned Non-Patent Document 8.

Physical properties: mp 169-171° C.

Example 31

2-Methyl-5-quinolin-3-yl-2-trifluoromethyl-2,3-dihydro-benzo[f][1,4]oxazepine (Compound No. B1-51)

Physical properties: amorphous $^1$H-NMR (300 MHz, $CDCl_3$) δ: 1.68 (s, 3H), 3.80 (d, 1H, J=12 Hz), 4.11 (d, 1H, J=12 Hz), 7.16-7.26 (m, 3H), 7.49-7.61 (m, 2H), 7.76-7.85 (m, 2H), 8.17 (d, 1H, J=8.4 Hz), 8.32 (d, 1H, J=2.1 Hz), 9.29 (d, 1H, J=2.1 Hz)

Example 32

2-Methyl-2-phenyl-5-quinolin-3-yl-2,3-dihydro-benzo[f][1,4]oxazepine (Compound No. B1-52)

Physical properties: mp 196-197° C.

Example 33

2-(4-Fluorobenzyl)-2-methyl-5-quinolin-3-yl-2,3-dihydro-benzo[f][1,4]oxazepine (Compound No. B1-53)

Physical properties: amorphous $^1$H-NMR (300 MHz, $CDCl_3$) δ: 1.33 (s, 3H), 3.10 (s, 2H), 3.47 (d, 1H, J=12.0 Hz), 3.76 (d, 1H, J=12.0 Hz), 6.97-7.05 (m, 2H), 7.14-7.26 (m, 3H), 7.32-7.38 (m, 2H), 7.45-7.60 (m, 2H), 7.74-7.85 (m, 2H), 8.17 (d, 1H, J=8.4 Hz), 8.33 (d, 1H, J=2.1 Hz), 9.63 (d, 1H, J=2.1 Hz)

Example 34

2,2-Dimethyl-5-quinolin-3-yl-2,3-dihydro-benzo[f][1,4]oxazepine-9-carbonitrile (Compound No. B1-54)

Physical properties: amorphous

Example 35

9-Methoxy-2,2-dimethyl-5-quinolin-3-yl-2,3-dihydro-benzo[f][1,4]oxazepine (Compound No. B1-55)

Physical properties: mp 153-155° C.

Example 36

5-(8-Fluoro-quinolin-3-yl)-2-methyl-2-trifluoromethyl-2,3-dihydro-benzo[f][1,4]oxazepine (Compound No. B1-56)

Physical properties: mp 103-105° C.

Example 37

9-Chloro-5-(5-chloro-quinolin-3-yl)-2,2-dimethyl-2,3-dihydro-benzo[f][1,4]oxazepine (Compound No. B1-57)

Physical properties: mp 157-159° C.

Example 38

9-Chloro-2,2-dimethyl-5-(5-methyl-quinolin-3-yl)-2,3-dihydro-benzo[f][1,4]oxazepine (Compound No. B1-58)

Physical properties: mp 160-162° C.

Example 39

9-Chloro-5-(6-chloro-quinolin-3-yl)-2,2-dimethyl-2,3-dihydro-benzo[f][1,4]oxazepine (Compound No. B1-59)

Physical properties: amorphous $^1$H-NMR (300 MHz, $CDCl_3$) δ: 1.56 (s, 6H), 3.66 (s, 2H), 7.03 (m, 1H), 7.13 (m, 1H), 7.59 (m, 1H), 7.69 (m, 1H), 7.79 (m, 1H), 8.09 (d, 1H, J=9.0 Hz), 8.18 (d, 1H, J=2.4 Hz), 9.25 (d, 1H, J=2.4 Hz)

Example 40

9-Chloro-2,2-dimethyl-5-(6-methylquinolin-3-yl)-2,3-dihydro-benzo[f][1,4]oxazepine (Compound No. B1-60)

Physical properties: mp 166-168° C.

Example 41

9-Chloro-5-(7-chloro-quinolin-3-yl)-2,2-dimethyl-2,3-dihydro-benzo[f][1,4]oxazepine (Compound No. B1-61)

Physical properties: amorphous $^1$H-NMR (300 MHz, $CDCl_3$) δ: 1.56 (s, 6H), 3.65 (s, 2H), 7.04 (m, 1H), 7.13 (m, 1H), 7.51-7.60 (m, 2H), 7.75 (d, 1H, J=8.7 Hz), 8.15 (d, 1H, J=1.8 Hz), 8.25 (d, 1H, J=1.5 Hz), 9.25 (d, 1H, J=2.1 Hz)

Example 42

9-Chloro-2,2-dimethyl-5-(7-methyl-quinolin-3-yl)-2,3-dihydro-benzo[f][1,4]oxazepine (Compound No. B1-62)

Physical properties: amorphous $^1$H-NMR (300 MHz, $CDCl_3$) δ: 1.55 (s, 6H), 2.58 (s, 3H), 3.63 (s, 2H), 7.03-7.13 (m, 2H), 7.39 (m, 1H), 7.57 (m, 1H), 7.69 (d, 1H, J=8.0 Hz), 7.91 (s, 1H), 8.22 (s, 1H), 9.18 (d, 1H, J=2.1 Hz)

Example 43

9-Chloro-5-(6,8-difluoro-quinolin-3-yl)-2,2-dimethyl-2,3-dihydro-benzo[f][1,4]oxazepine (Compound No. B1-63)

Physical properties: amorphous $^1$H-NMR (300 MHz, $CDCl_3$) δ: 1.55 (s, 6H), 3.66 (s, 2H), 7.06 (m, 1H), 7.13 (m, 1H), 7.24-7.31 (m, 2H), 7.59 (m, 1H), 8.24 (s, 1H), 9.23 (d, 1H, J=1.8 Hz)

Example 44

9-Chloro-2,2-dimethyl-5-quinolin-3-yl-2,3-dihydro-benzo[f][1,4]oxazepine hydrochloride salt (Compound No. B1-64)

Physical properties: mp 149-151° C.

Example 45

9-Chloro-2,2-dimethyl-5-quinolin-3-yl-2,3-dihydro-benzo[f][1,4]oxazepine trifluoroacetic acid salt (Compound No. B1-65)

Physical properties: mp 129-131° C.

Example 46

9-Fluoro-5-(8-fluoro-quinolin-3-yl)-2,2-dimethyl-2,3-dihydro-benzo[f][1,4]oxazepine trifluoroacetic acid salt (Compound No. B1-66)

Physical properties: mp 174-176° C.

Example 47

9-Fluoro-5-(8-fluoro-quinolin-3-yl)-2,2-dimethyl-2,3-dihydro-benzo[f][1,4]oxazepine hydrochloride salt (Compound No. B1-67)

Physical properties: mp 164-166° C.

Example 48

2-Cyclopropyl-2-methyl-5-quinolin-3-yl-2,3-dihydro-benzo[f][1,4]oxazepine (Compound No. B1-70)

Physical properties: amorphous $^1$H-NMR (300 MHz, $CDCl_3$) δ: 0.48-0.61 (m, 4H), 1.24-1.38 (m, 4H), 3.69 (d, 1H, J=11.6 Hz), 3.81 (d, 1H, J=11.6 Hz), 7.10-7.83 (m, 7H), 8.16 (d, 1H, J=8.3 Hz), 8.31 (d, 1H, J=2.1 Hz), 9.26 (d, 1H, J=2.1 Hz)

Example 49

5-Quinolin-3-yl-2,3-dihydro-benzo[f][1,4]oxazepine-2-spiro-cyclopropane (Compound No. B1-72)

Physical properties: mp 102-104° C.

Example 50

9-Benzyl-2,2-dimethyl-5-quinolin-3-yl-2,3-dihydro-benzo[f][1,4]oxazepine (Compound No. B1-74)

Physical properties: amorphous $^1$H-NMR (300 MHz, $CDCl_3$) δ: 1.53 (s, 6H), 3.61 (s, 2H), 4.13 (s, 2H), 6.95-7.85 (m, 11H), 8.15 (d, 1H, J=8.1 Hz), 8.28 (d, 1H, J=2.1 Hz), 9.28 (d, 1H, J=2.1 Hz)

Example 51

7-Chloro-2,2-dimethyl-5-quinolin-3-yl-2,3-dihydro-benzo[f][1,4]oxazepine (Compound No. B1-77)

Physical properties: amorphous $^1$H-NMR (300 MHz, $CDCl_3$) δ: 1.48 (s, 6H), 3.61 (s, 2H), 7.09 (d, 1H, J=8.7 Hz), 7.15 (d, 1H, J=2.7 Hz), 7.44 (dd, 1H, J=8.7, 2.7 Hz), 7.56-7.62 (m, 1H), 7.75-7.87 (m, 2H), 8.17 (d, 1H, J=8.4 Hz), 8.31 (d, 1H, J=2.4 Hz), 9.27 (d, 1H, J=2.1 Hz)

Example 52

5-(8-Fluoro-quinolin-3-yl)-2,2,9-trimethyl-2,3-dihydro-benzo[f][1,4]oxazepine (Compound No. B1-79)

Physical properties: mp 151-153° C.

Example 53

2,2-Dimethyl-9-phenoxy-5-quinolin-3-yl-2,3-dihydro-benzo[f][1,4]oxazepine (Compound No. B1-82)

Physical properties: amorphous $^1$H-NMR (300 MHz, $CDCl_3$) δ: 1.48 (s, 6H), 3.67 (s, 2H), 6.9-7.9 (m, 11H), 8.17 (d, 1H, J=8.1 Hz), 8.36 (d, 1H, J=1.8 Hz), 9.31 (d, 1H, J=2.1 Hz)

Example 54

11-Quinolin-3-yl-dibenzo[b,f][1,4]oxazepine (Compound No. B1-83)

Physical properties: mp 182-184° C.

Example 55

5-Quinolin-3-yl-benzo[f][1,4]oxazepin-3-one (Compound No. B1-84)

Physical properties: mp 169-170° C.

Example 56

8-Fluoro-3,3-dimethyl-5-quinolin-3-yl-2,3-dihydro-benzo[f][1,4]oxazepine (Compound No. B1-85)

Physical properties: mp 133-135° C.

Example 57

6-Fluoro-5-quinolin-3-yl-2,3-dihydro-benzo[f][1,4]oxazepine (Compound No. B1-86)

Physical properties: mp 126-128° C.

Example 58

4-Fluoro-6,6-dimethyl-9-quinolin-3-yl-6,7-dihydro-5-thia-8-aza-benzocycloheptene (Compound No. B2-14)

Physical properties: mp 119-122° C.

Example 59

4-Fluoro-9-(8-fluoro-quinolin-3-yl)-6,6-dimethyl-6,7-dihydro-5-thia-8-aza-benzocycloheptene (Compound No. B2-15)

Physical properties: mp 179-181° C.

Example 60

6,6-Dimethyl-9-quinolin-3-yl-6,7-dihydro-5-thia-8-aza-benzocycloheptene 5-oxide (Compound No. B2-16)

Physical properties: mp 118-120° C.

Example 61

9-Chloro-5-(5,6-dimethyl-pyridin-3-yl)-2,3-dihydro-benzo[f][1,4]oxazepine (Compound No. A1-21)

Physical properties: mp 142-143° C.

Example 62

9-Chloro-5-(6,7-dihydro-5H-[1]pyridin-3-yl)-2,2,3,3-tetramethyl-2,3-dihydro-benzo[f][1,4]oxazepine (Compound No. A1-22)

Physical properties: mp 132-133° C.

Example 63

5-Quinolin-3-yl-4,5-dihydro-benzo[f][1,4]oxazepin-3-one (Compound No. B4-46)

Physical properties: mp 225-227° C.

Example 64

9-Fluoro-5-(8-fluoro-quinolin-3-yl)-2,2-dimethyl-2,3,4,5-tetrahydro-benzo[f][1,4]oxazepine (Compound No. B4-47)

Physical properties: mp 130-131° C.

Example 65

4-Ethyl-9-fluoro-5-(8-fluoro-quinolin-3-yl)-2,2-dimethyl-2,3,4,5-tetrahydro-benzo[f][1,4]oxazepine (Compound No. B4-48)

Physical properties: mp 117-118° C.

Example 66

9-Chloro-5-(8-fluoro-quinolin-3-yl)-2,2-dimethyl-2,3,4,5-tetrahydro-benzo[f][1,4]oxazepine (Compound No. B4-49)

Physical properties: mp 133-134° C.

Example 67

4-Benzyl-9-chloro-5-(8-fluoro-quinolin-3-yl)-2,2-dimethyl-2,3,4,5-tetrahydro-benzo[f][1,4]oxazepine (Compound No. B4-50)

Physical properties: mp 138-141° C.

Example 68

9-Fluoro-5-(8-fluoro-quinolin-3-yl)-2,2-dimethyl-2,3-dihydro-5H-benzo[f][1,4]oxazepine-4-carbaldehyde (Compound No. B4-51)

Physical properties: mp 131-133° C.

Example 69

1-[9-Fluoro-5-(8-fluoro-quinolin-3-yl)-2,2-dimethyl-2,3-dihydro-5H-benzo[f][1,4]oxazepin-4-yl]-ethanone (Compound No. B4-52)

Physical properties: mp 132-134° C.

Example 70

2,2-Dimethyl-5-quinolin-3-yl-4,5-dihydro-benzo[f][1,4]oxazepin-3-one (Compound No. B4-53)

Physical properties: mp 225-227° C.

Example 71

8b-(8-Fluoro-quinolin-3-yl)-3,3-dimethyl-2,3-dihydro-8bH-1,4-dioxa-1a-aza-benzo[a]cyclopropa[c]cycloheptene (Compound No. B6-34)

This compound was synthesized with reference to Method C described in the aforementioned Patent Document 1 by using 5-(8-fluoro-quinolin-3-yl)-2,2-dimethyl-2,3-dihydro-benzo[f][1,4]oxazepine for the starting material.

Physical properties: mp 113-115° C.

Example 72

5-(8-Fluoro-quinolin-3-yl)-2,2-dimethyl-2,3-dihydro-benzo[f][1,4]oxazepine 4-oxide (Compound No. B5-34)

This compound was synthesized with reference to Method D described in the aforementioned Patent Document 1 by using 8b-(8-fluoro-quinolin-3-yl)-3,3-dimethyl-2,3-dihydro-8bH-1,4-dioxa-1a-aza-benzo[a]cyclopropa[c]cycloheptene for the starting material.

Physical properties: mp 179-181° C.

Production Intermediate Synthesis [Example 73]

8-Fluoro-3-quinoline boronic acid (Compound No. C1-1)

An anhydrous THF solution (130 mL) was added to a 300 mL flask using a syringe after carrying out nitrogen replacement followed by cooling the reaction container in a salt-ice bath. Subsequently, a THF solution of 0.91 M n-BuMgCl (20.72 mL, 18.86 mmol) and a hexane solution of 2.63 M n-BuLi (14.73 mL, 38.74 mmol) were sequentially added followed by stirring for 30 minutes at that temperature. 8-Fluoro-3-iodoquinoline (13.92 g, 50.98 mmol) was added to this solution as a solid, and after stirring for 1.5 hours at the same temperature, B (IMe)$_3$ (6.36 g, 61.18 mmol) was added followed by additionally stirring for 2 hours. $H_2O$ (27.8 g) and 1 M NaOH (27.8 g) were sequentially added to this reaction solution followed by stirring for 30 minutes at room temperature. The pH of the reaction solution was then adjusted to 6 to 7 using 1 M aqueous HCl solution, this solution was extracted with ethyl acetate (300 mL×2), and the combined organic layer was washed with brine (100 mL) followed by drying with magnesium sulfate. After filtering, the solvent was distilled off under reduced pressure and the resulting residue was sequentially washed with hexane and diethyl ether to obtain 8.89 g (91%) of the target compound in the form of a beige solid. The 8-fluoro-3-iodoquinoline used in the reaction was prepared with reference to the method described in the aforementioned Non-Patent Document 9 and Patent Document 3.

Physical properties: mp 198-201° C.

Example 74

3-Quinoline boronic acid triol salt (Compound No. C2-12) 8.65 g (50 mmol) of 3-quinoline boronic acid and 6.0 g (50 mmol) of 1,1,1-tris(hydroxymethyl)ethane were added to 50 mL of toluene followed by heating and refluxing for 1 hour. After cooling the reaction liquid to 50° C., 2.66 g (47.5 mmol) of potassium hydroxide were gradually added followed by dehydrating with a Dean-Stark apparatus while further heating and refluxing for 4 hours. After cooling the reaction liquid to room temperature, the precipitated crystals were filtered out and sequentially washed with 50 mL of toluene and 20 mL of acetone followed by drying for 12 hours under reduced pressure to obtain 10.4 g (yield: 71%) of the triol salt of the target compound.

$^1$H-NMR (300 MHz, DMSO) δ: 0.53 (s, 3H), 3.66 (s, 6H), 7.37-7.56 (m, 2H), 7.73-7.85 (m, 2H), 8.13 (s, 1H), 8.83 (d, 1H, J=1.5 Hz)

The compound of Compound No. C2-4 was also able to be produced using a similar method.

$^1$H-NMR (300 MHz, DMSO) δ: 0.54 (s, 3H), 3.69 (s, 6H), 7.25-7.40 (m, 2H), 7.56-7.59 (m, 1H), 8.16 (s, 1H), 8.93 (s, 1H)

Example 75

Synthesis Example Using Triol Salt (Variation of Example 51)

(Step 1)

Synthesis of trifluoromethanesulfonic acid 7-chloro-2,2-dimethyl-3,4-dihydro-2H-benzo[f][1,4]oxazepin-5-yl ester 1.6 g (7.09 mmol) of 7-chloro-2,2-dimethyl-3,4-dihydro-2H-benzo[f][1,4]oxazepin-5-one were dissolved in 50 mL of dichloromethane followed by dropping 3.0 g (10.6 mmol) of trifluoromethanesulfonic acid anhydride while cooling to −10° C. and stirring for 1 hour at the same temperature. Moreover, 1.13 g (10.6 mmol) of 2,6-lutidine were added while cooling to −10° C. and stirred for 1 hour followed by pouring the reaction liquid into ice water and extracting with chloroform. After washing the organic layer with saturated saline, the solvent was distilled off under reduced pressure followed by purifying the resulting residue by silica gel column chromatography (developing solvent; n-hexane:ethyl acetate=9:1) to obtain 2.25 g (yield: 89%) of the target compound.

(Step 2)

Production of 7-chloro-2,2-dimethyl-5-(3-quinolinyl)-2,3-dihydro-benzo[f][1,4]oxazepine (Compound No. B1-77)

1.33 g (3.76 mmol) of 3-quinoline boronic acid triol salt (compound of Compound No. C2-12), 1.0 g of trifluoromethanesulfonic acid 7-chloro-2,2-dimethyl-3,4-dihydro-2H-benzo[f][1,4]oxazepin-5-yl ester and 0.86 g (0.68 mmol) of $Pd(PPh_3)_4$ were added to 40 mL of toluene and after carrying out nitrogen replacement on the reaction solution, the reaction solution was refluxed while heating for 14 hours. After cooling the reaction solution to room temperature, the reaction solution was poured into ice water and extracted with ethyl acetate. After washing the organic layer with saturated saline, the solvent was distilled off under reduced pressure and the resulting residue was purified by silica gel column chromatography (developing solvent; n-hexane:ethyl acetate=3:1) to obtain 0.1 g (yield: 10%) of the target compound.

PREPARATIONS

Next, although the following indicates some examples of the fungicide of the present invention, the additives and addition ratios are not limited to these examples, but rather can be varied over a wide range. In addition, the term "parts" indicated in the preparation examples refers to parts by weight.

Preparation Example 1

Wettable Powder

| | |
|---|---|
| Compound of present invention | 40 parts |
| Clay | 48 parts |
| Sodium dioctylsulfosuccinate | 4 parts |
| Sodium lignin sulfonate | 8 parts |

The above components are uniformly mixed and finely crushed to obtain a wettable powder containing 40% of the active ingredient.

Preparation Example 2

Emulsion

| | |
|---|---|
| Compound of present invention | 10 parts |
| Solvesso 200 | 53 parts |
| Cyclohexanone | 26 parts |
| Calcium dodecylbenzenesulfonate | 1 part |
| Polyoxyethylene alkyl allyl ether | 10 parts |

The above components are mixed and dissolved to obtain an emulsion containing 10% of the active ingredient.

Preparation Example 3

Powder

| | |
|---|---|
| Compound of present invention | 10 parts |
| Clay | 90 parts |

The above components are uniformly mixed and finely crushed to obtain a powder containing 10% of the active ingredient.

Preparation Example 4

Granules

| | |
|---|---|
| Compound of present invention | 5 parts |
| Clay | 73 parts |
| Bentonite | 20 parts |
| Sodium dioctylsulfosuccinate | 1 part |
| Potassium phosphate | 1 part |

The above components are crushed and mixed well followed by the addition of water, mixing well, granulating and drying to obtain granules containing 5% of the active ingredient.

Preparation Example 5

Suspension

| | |
|---|---|
| Compound of present invention | 10 parts |
| Polyoxyethylene alkyl allyl ether | 4 parts |
| Sodium polycarbonate | 2 parts |
| Glycerin | 10 parts |
| Xanthan gum | 0.2 parts |
| Water | 73.8 parts |

The above components are mixed followed by wet-crushing to a particle diameter of 3 microns or less to obtain a suspension containing 10% of the active ingredient.

Preparation Example 6

Water Dispersible Granules

| | |
|---|---|
| Compound of present invention | 40 parts |
| Clay | 36 parts |
| Potassium chloride | 10 parts |
| Sodium alkylbenzenesulfonate | 1 part |
| Sodium lignin sulfonate | 8 parts |
| Formaldehyde condensation product of sodium alkylbenzenesulfonate | 5 parts |

The above components are uniformly mixed and finely crushed followed by adding a suitable amount of water and mixing to form a clay-like mixture. The clay-like mixture is granulated and dried to obtain water dispersible granules containing 40% of the active ingredient.

TEST

Test Example 1

Apple Scab Control Test

Emulsions of compounds of the present invention were sprayed at an active ingredient concentration of 100 ppm onto apple seedlings (variety: Ralls Janet, leaf stage: 3 to 4) cultivated in unglazed pots. After allowing to air-dry at room temperature, the seedlings were inoculated with conidiospores of apple scab pathogen (*Venturia inaequalis*) followed by holding for 2 weeks indoors at 20° C. and high humidity using a 12 hour light/dark cycle. The appearance of lesions on the leaves was compared with untreated seedlings to determine control effects.

As a result, the following compounds demonstrated superior control values of 75% or more:

compound numbers (corresponding to the compound numbers listed in Tables 1 to 12): A1-19, A1-20, B1-1, B1-3, B1-9, B1-11, B1-29 to B1-49, B1-51, B1-53, B1-54, B1-56, B1-62 to 31-67, B1-70, B1-79, B1-82, B2-6, B2-13 to B2-15, B4-47 to B4-49, B5-34, B6-34.

Test Example 2

Cucumber Gray Mold Control Test

Emulsions of compounds of the present invention were sprayed at an active ingredient concentration of 100 ppm onto cucumber seedlings (variety: Sagami Hanjiro, leaf stage: cotyledon) cultivated in unglazed pots. After allowing to air-dry at room temperature, the seedlings were drip-inoculated with conidiospore suspensions of cucumber gray mold pathogen (*Botrytis cinerea*) followed by holding in the dark for 4 days indoors at 20° C. and high humidity. The appearance of lesions on the leaves was compared with untreated seedlings to determine control effects.

As a result, the following compounds demonstrated superior control values of 75% or more:

compound numbers: A1-19 to A1-22, B1-3, B1-9, B1-11, B1-29 to B1-62, B1-63 to B1-67, B1-70, B1-72, B1-74, B1-77, B1-79, B1-82, B1-84, B2-6, B2-13 to B2-15, B4-47 to B4-51, B4-50, B5-34, B6-34.

Test Example 3

Rice Blast Soil Irrigation Test

Rice seedlings (variety: Hitomebore, leaf stage: 1) were cultured in pots filled with commercially available potting soil, and emulsions of compounds of the present invention were dripped into soil at an active ingredient concentration of 200 ppm. After managing the seedlings under inundated conditions for 14 days, seedlings were inoculated by spraying with conidiospore suspensions of rice blast pathogen (*Pyricularia oryzae*) followed by holding in the dark for 2 days indoors at 25° C. and high humidity and then holding for 8 days indoors at 25° C. using a 12 hour light/dark cycle. The appearance of lesions on the leaves was compared with untreated seedlings, and control effects were evaluated based on the criteria indicated below.

A: Control value of 60% or more

B: Control value of 40 to less than 60%

As a result, control values of the following compounds were evaluated as A:

compound numbers: A1-20, B1-1, B1-38, 31-39.

In addition, control values of the following compounds were evaluated as B:

compound numbers: B1-3, B1-37.

Test Example 4

Cucumber *Fusarium* Wilt Seedling Treatment Test

Cucumber seedlings (variety: Sagami Hanjiro) infected with cucumber *fusarium* wilt pathogen (*Fusarium oxysporum*) were treated emulsions of compounds of the present invention having an active ingredient concentration of 1 g/kg of seedlings. The seeds were then sown and the degree of disease onset was compared with untreated seedlings 3 weeks later to determine control effects.

As a result, the following compounds demonstrated superior control values of 75% or more:

compound numbers: A1-19, B1-1, B1-3, B1-9, B1-11, B1-34, B1-37 to B1-39, B2-6.

The invention claimed is:

1. A nitrogen-containing heterocyclic compound represented by formula (IV), or a salt thereof:

(IV)

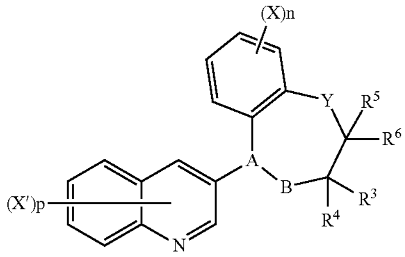

wherein, $R^3$, $R^4$, $R^5$, and $R^6$ each independently represents a hydrogen atom, unsubstituted or substituted $C_{1-20}$ alkyl group, unsubstituted or substituted $C_{2-20}$ alkenyl group, unsubstituted or substituted $C_{2-20}$ alkynyl group, unsubstituted or substituted $C_{3-20}$ cycloalkyl group, unsubstituted or substituted $C_{4-20}$ cycloalkenyl group, unsubstituted or substituted $C_{8-20}$ cycloalkynyl group, unsubstituted or substituted $C_{6-10}$ aryl group, unsubstituted or substituted heterocyclic group, unsubstituted or substituted $C_{1-20}$ acyl group, unsubstituted or substituted (1-imino)$C_{1-20}$ alkyl group, unsubstituted or substituted hydroxyl group, unsubstituted or substituted amino group, unsubstituted or substituted mercapto group, unsubstituted or substituted sulfonyl group, halogeno group or cyano group;

a plurality of $R^3$ ,$R^4$, $R^5$, and $R^6$ may be selected and bond together to form an unsubstituted or substituted 3- to 8-membered ring;

$R^3$ and $R^4$, or $R^5$ and $R^6$ may bond together to form an oxo group, thioxo group or unsubstituted or substituted imino group;

A-B, in which A represents a carbon atom and B represents a nitrogen atom, represents the formula: C═N, the formula: $CR^7$—$NR^8$, the following formula (II) or the following formula (III);

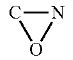
(II)

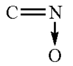
(III)

$R^7$ represents a hydrogen atom, unsubstituted or substituted $C_{1-20}$ alkyl group, unsubstituted or substituted $C_{2-20}$ alkenyl group, unsubstituted or substituted $C_{2-20}$ alkynyl group, unsubstituted or substituted $C_{1-20}$ acyl group, unsubstituted or substituted hydroxyl group, unsubstituted or substituted amino group, unsubstituted or substituted mercapto group, halogeno group or cyano group;

$R^8$ represents a hydrogen atom, unsubstituted or substituted $C_{1-20}$ alkyl group, unsubstituted or substituted $C_{2-20}$ alkenyl group, unsubstituted or substituted $C_{2-20}$ alkynyl group, or unsubstituted or substituted $C_{1-20}$ acyl group;

Y represents an oxygen atom, sulfur atom or sulfinyl group;

X and X' each independently represents an unsubstituted or substituted $C_{1-20}$ alkyl group, unsubstituted or substituted $C_{2-20}$ alkenyl group, unsubstituted or substituted $C_{2-20}$ alkynyl group, unsubstituted or substituted $C_{3-20}$ cycloalkyl group, unsubstituted or substituted $C_{4-20}$ cycloalkenyl group, unsubstituted or substituted $C_{8-20}$ cycloalkynyl group, unsubstituted or substituted $C_{6-10}$ aryl group, unsubstituted or substituted heterocyclic group, unsubstituted or substituted $C_{1-20}$ acyl group, unsubstituted or substituted (1-imino) $C_{1-20}$ alkyl group, unsubstituted or substituted hydroxyl group, unsubstituted or substituted amino group, unsubstituted or substituted mercapto group, unsubstituted or substituted sulfonyl group, halogeno group, cyano group or nitro group;

p represents an integer of 0 to 6; and, n represents an integer of 0 to 4.

2. The nitrogen-containing heterocyclic compound or salt thereof according to claim 1, wherein the formula (IV) is represented by formula (IX):

(IX)

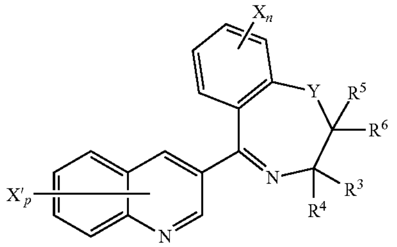

wherein, X, X', n, p, $R^3$ ,$R^4$, $R^5$, and $R^6$ and Y are the same as defined in claim 1.

3. A fungicidal composition for agricultural and horticultural use, comprising: at least one of the nitrogen-containing heterocyclic compound or salt thereof according to claim 1 or 2 as an active ingredient thereof.

* * * * *